(12) United States Patent
Honjo et al.

(10) Patent No.: US 11,138,723 B2
(45) Date of Patent: Oct. 5, 2021

(54) ANALYZING APPARATUS AND ANALYZING METHOD

(71) Applicant: CANON MEDICAL SYSTEMS CORPORATION, Otawara-shi (JP)

(72) Inventors: Yasunori Honjo, Kawasaki (JP); Yu Igarashi, Kawasaki (JP); Masaki Watanabe, Kawasaki (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 15/656,599

(22) Filed: Jul. 21, 2017

(65) Prior Publication Data
US 2018/0025492 A1 Jan. 25, 2018

(30) Foreign Application Priority Data

Jul. 22, 2016 (JP) .............................. JP2016-144697
Jul. 19, 2017 (JP) .............................. JP2017-140280

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/7271* (2013.01); *A61B 8/485* (2013.01); *A61B 8/5223* (2013.01); *G06K 9/2081* (2013.01); *G06K 9/4642* (2013.01); *G06T 7/11* (2017.01); *G06T 7/187* (2017.01); *G06T 11/60* (2013.01); *A61B 5/7475* (2013.01); *G06T 2207/10132* (2013.01); *G06T 2207/20021* (2013.01);
(Continued)

(58) Field of Classification Search
CPC combination set(s) only.
See application file for complete search history.

(56) References Cited

U.S. PATENT DOCUMENTS 7,713,206 B2 * 5/2010 Karasawa ................ A61B 8/14
600/443
9,060,737 B2 * 6/2015 Matsumura .............. A61B 8/08
(Continued)

FOREIGN PATENT DOCUMENTS

| JP | 2001-54520 | 2/2001 |
|---|---|---|
| JP | 2012-077579 A | 4/2012 |
| JP | 2015-92938 | 5/2015 |

OTHER PUBLICATIONS

Japanese Office Action dated Apr. 27, 2021, issued in Japanese Patent Application No. 2017-140280.

*Primary Examiner* — Anand P Bhatnagar
(74) *Attorney, Agent, or Firm* — Oblon, McClelland, Maier & Neustadt, L.L.P.

(57) ABSTRACT

An analyzing apparatus according to an embodiment includes processing circuitry. The processing circuitry is configured to calculate a tissue characteristic parameter value with respect to each of a plurality of positions within a region of interest, by analyzing a result of a scan performed on a patient. The processing circuitry is configured to determine a measurement region in the region of interest by performing an analysis while using the tissue characteristic parameter values. The processing circuitry is configured to calculate a statistic value of the tissue characteristic parameter values in the measurement region.

37 Claims, 13 Drawing Sheets

(51) Int. Cl.
*G06T 11/60* (2006.01)
*G06K 9/20* (2006.01)
*A61B 5/00* (2006.01)
*A61B 8/08* (2006.01)
*G06K 9/46* (2006.01)
*G06T 7/187* (2017.01)

(52) U.S. Cl.
CPC ............... *G06T 2207/20081* (2013.01); *G06T 2207/30004* (2013.01); *G06T 2207/30024* (2013.01); *G06T 2210/41* (2013.01)

(56) References Cited

U.S. PATENT DOCUMENTS

| | | | | |
|---|---|---|---|---|
| 9,072,493 | B1* | 7/2015 | Yoshikawa | G01S 7/52074 |
| 9,084,559 | B2* | 7/2015 | Sumi | A61B 8/483 |
| 9,311,704 | B2* | 4/2016 | Waki | A61B 8/5207 |
| 9,913,976 | B2* | 3/2018 | Wagner | A61N 1/36017 |
| 10,143,446 | B2* | 12/2018 | Tang | A61B 8/485 |
| 10,342,514 | B2* | 7/2019 | Kanayama | G01S 7/52042 |
| 2009/0143676 | A1* | 6/2009 | Matsumura | A61B 8/08 600/438 |
| 2010/0246908 | A1* | 9/2010 | Yokono | G06K 9/4642 382/128 |
| 2013/0066204 | A1* | 3/2013 | Fan | A61B 8/5223 600/438 |
| 2015/0087976 | A1* | 3/2015 | Fan | A61B 8/5207 600/438 |
| 2015/0119712 | A1* | 4/2015 | Tanigawa | G01S 15/8915 600/438 |
| 2015/0133782 | A1 | 5/2015 | Yoshikawa | |
| 2015/0141822 | A1* | 5/2015 | Miyauchi | A61B 8/461 600/438 |
| 2015/0164476 | A1* | 6/2015 | Kong | A61B 8/5207 600/438 |
| 2015/0173719 | A1* | 6/2015 | Tanigawa | A61B 8/5207 600/438 |
| 2015/0173720 | A1 | 6/2015 | Yoshikawa | |
| 2015/0279025 | A1* | 10/2015 | Waki | G06T 11/60 382/103 |

* cited by examiner

SEGMENTED REGIONS (SMALL)  SEGMENTED REGIONS (MEDIUM)  SEGMENTED REGIONS (LARGE)

ANALYZING APPARATUS AND ANALYZING METHOD

CROSS-REFERENCE TO RELATED APPLICATIONS

This application is based upon and claims the benefit of priority from Japanese Patent Application No. 2016-144697, filed on Jul. 22, 2016, and Japanese Patent Application No. 2017-140280, filed on Jul. 19, 2017; the entire contents of which are incorporated herein by reference.

FIELD

Embodiments described herein relate generally to an analyzing apparatus and an analyzing method.

BACKGROUND

In recent years, various types of medical image diagnosis apparatuses are configured not only to express, in an image, a tomographic view of a tissue in a patient's body, but also to express, in an image, a parameter indicating a characteristic of a tissue (which hereinafter may be referred to as "tissue characteristic parameter"). For example, an ultrasound diagnosis apparatus uses technology called elastography by which a distribution of firmness levels of a tissue is expressed in an image.

Further, when a tissue characteristic parameter is expressed in an image, quantitative information is provided by measuring parameter values in a desired region included in the image. For example, by using elastography implemented by an ultrasound diagnosis apparatus, fibrosis of the liver is expressed in an image, so as to categorize each of fibrosis regions to be in one of fibrosis stages according to the degree of firmness of the region.

DETAILED DESCRIPTION

It is an object of the present disclosure to provide an analyzing apparatus and an analyzing method that are able to analyze a tissue characteristic with an excellent level of precision.

An analyzing apparatus according to an embodiment includes processing circuitry. The processing circuitry is configured to calculate a tissue characteristic parameter value with respect to each of a plurality of positions within a region of interest, by analyzing a result of a scan performed on a patient. The processing circuitry is configured to determine a measurement region in the region of interest by performing an analysis while using the tissue characteristic parameter values. The processing circuitry is configured to calculate a statistic value of the tissue characteristic parameter values in the measurement region.

Exemplary embodiments of an analyzing apparatus and an analyzing computer program will be explained with reference to the accompanying drawings. In the embodiments described below, an ultrasound diagnosis apparatus will be explained as an example of the analyzing apparatus. However, possible embodiments are not limited to this example. For instance, as the analyzing apparatus, other medical image diagnosis apparatuses besides ultrasound diagnosis apparatuses are also applicable, such as X-ray diagnosis apparatuses, X-ray Computed Tomography (CT) apparatuses, Magnetic Resonance Imaging (MRI) apparatuses, Single Photon Emission Computed Tomography (SPECT) apparatuses, Positron Emission computed Tomography (PET) apparatuses, SPECT-CT apparatuses in which a SPECT apparatus and an X-ray CT apparatus are integrated together, PET-CT apparatuses in which a PET apparatus and an X-ray CT apparatus are integrated together, or a group made up of any of these apparatuses. Further, as the analyzing apparatus, not only medical image diagnosis apparatuses, but also arbitrary medical information processing apparatuses are applicable.

First Embodiment

Figure 1:
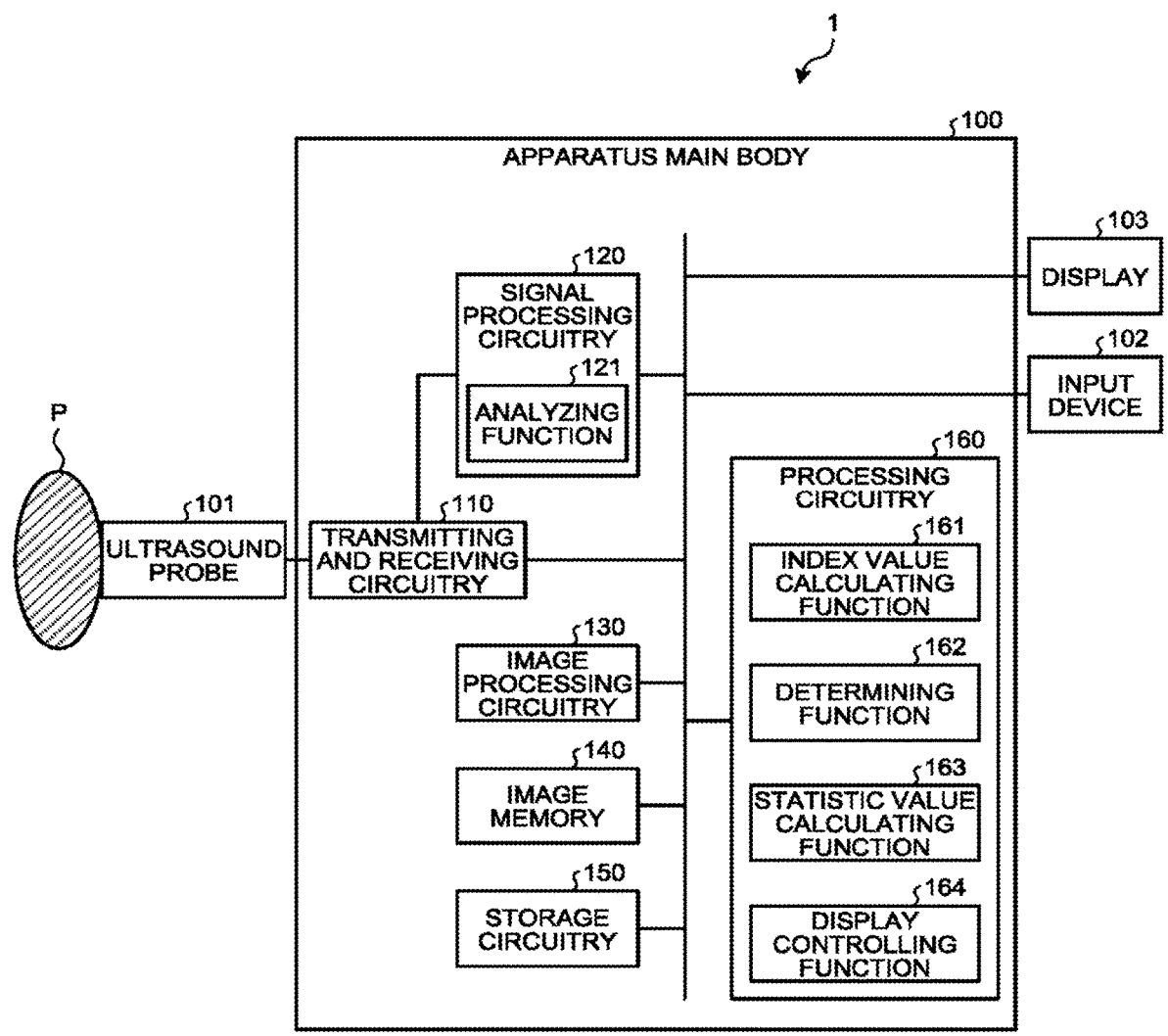
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input device 102, and a display 103. The ultrasound probe 101, the input device 102, and the display 103 are connected to the apparatus main body 100.

In this situation, an examined subject (hereinafter, "patient") P is not included in the configuration of the ultrasound diagnosis apparatus 1.

The ultrasound probe 101 includes a plurality of transducer elements (e.g., piezoelectric transducer elements). Each of the plurality of transducer elements is configured to generate an ultrasound wave on the basis of a drive signal supplied thereto from transmitting and receiving circuitry 110 (explained later) included in the apparatus main body 100. Further, the plurality of transducer elements included in the ultrasound probe 101 are configured to receive reflected waves from the patient P and to convert the reflected waves into an electrical signal. Further, the ultrasound probe 101 includes matching layers provided for the transducer elements, as well as a backing member or the like that prevents the ultrasound waves from propagating rearward from the transducer elements.

When an ultrasound wave is transmitted the ultrasound probe 101 to the patient P, the transmitted ultrasound wave is repeatedly reflected on a surface of discontinuity of acoustic impedances at a tissue in the body of the patient P and is received as a reflected-wave signal (an echo signal) by each of the plurality of transducer elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The first embodiment is applicable to a situation where the ultrasound probe 101 illustrated in FIG. 1 is a one-dimensional ultrasound probe in which a plurality of piezoelectric transducer elements are arranged in a row, a one-dimensional ultrasound probe in which a plurality of piezoelectric transducer elements arranged in a row are mechanically swayed, or a two-dimensional ultrasound probe in which a plurality of piezoelectric transducer elements are two-dimensionally arranged in a grid formation.

The input device 102 includes a mouse, a keyboard, a button, a panel switch, a touch command screen, a foot switch a trackball, a joystick, and/or the like. The input device 102 is configured to receive various types of setting requests from an operator of the ultrasound diagnosis apparatus 1 and to transfer the received various types of setting requests to the apparatus main body 100.

The display 103 is configured to display a Graphical User Interface (GUI) used by the operator of the ultrasound diagnosis apparatus 1 to input the various types of setting requests through the input device 102 and to display ultrasound image data generated by the apparatus main body 100 or the like.

The apparatus main body 100 is an apparatus configured to generate the ultrasound image data on the basis of the reflected-wave signals received by the ultrasound probe 101. As illustrated in FIG. 1, the apparatus main body 100 includes the transmitting and receiving circuitry 110, signal processing circuitry 120, image processing circuitry 130, an image memory 140, storage circuitry 150, and processing circuitry 160. The transmitting and receiving circuitry 110, the signal processing circuitry 120, the image processing circuitry 130, the image memory 140, the storage circuitry 150, and the processing circuitry 160 are connected to one another so as to be able to communicate with one another.

The transmitting and receiving circuitry 110 includes a pulser generator, a transmission delay unit, a pulser, and the like and is configured to supply the drive signal to the ultrasound probe 101. The pulse generator is configured to repeatedly generate a rate pulse used for forming transmission ultrasound wave, at a predetermined rate frequency. Further, the transmission delay unit applies a delay period that is required to converge the ultrasound wave generated by the ultrasound probe 101 into the form of a beam and to determine transmission directionality and that corresponds to each of the piezoelectric transducer elements, to each of the rate pulses generated by the pulse generator. Further, the pulser applies the drive signal (a drive pulse) to the ultrasound probe 101 with timing based on the rate pulses. In other words, by varying the delay periods applied to the rate pulses, the transmission delay unit arbitrarily adjusts the transmission directions of the ultrasound waves transmitted from the surfaces of the piezoelectric transducer element.

The transmitting and receiving circuitry 110 has a function to be able instantly change the transmission frequency, the transmission drive voltage, and the like, for the purpose of executing a predetermined scanning sequence on the basis of an instruction from the processing circuitry 160 (explained later). In particular, the configuration to change the transmission drive voltage is realized by using a linear-amplifier-type transmission circuitry of which the value can be instantly switched or by using a mechanism configured to electrically switch between a plurality of power source units.

Further, the transmitting and receiving circuitry 110 includes a pre-amplifier, an Analog/Digital (A/D) converter, a reception delay unit, an adder, and the like. The transmitting and receiving circuitry 110 is configured to generate reflected-wave data by performing various types of processes on the reflected-wave signals received by the ultrasound probe 101. The pre-amplifier is configured to amplify the reflected-wave signal for each of the channels. The A/D converter is configured to apply an A/D conversion to the amplified reflected-wave signals. The reception delay unit is configured to apply a delay period required to determine the reception directionality. The adder is configured to generate the reflected-wave data by performing an adding process on the reflected-wave signals processed by the reception delay unit. As a result of the adding process performed by the adder, reflected components from the direction corresponding to the reception directionality of the reflected-wave signals are emphasized, so that a comprehensive beam for transmitting and receiving the ultrasound wave is formed on the basis of the reception directionality and the transmission directionality.

When a two-dimensional region of the patient P is to be scanned, the transmitting and receiving circuitry 110 causes the ultrasound probe 101 to transmit an ultrasound beam in two-dimensional directions. Further, the transmitting and receiving circuitry 110 generates two-dimensional reflected-wave data from reflected-wave signals received by the ultrasound probe 101. In contrast, when a three-dimensional region of the patient P is to be scanned, the transmitting and receiving circuitry 110 causes the ultrasound probe 101 to transmit an ultrasound beam in three-dimensional directions. Further, the transmitting and receiving circuitry 110 generates three-dimensional reflected-wave data from reflected-wave signals received by the ultrasound probe 101.

For example, the signal processing circuitry 120 is configured to generate data (B-mode data) in which the signal intensity at each sampling point is expressed as a level of brightness, by performing a logarithmic amplifying process, an envelope detecting process, or the like on the reflected-wave data received from the transmitting and receiving circuitry 110. The B-mode data generated by the signal processing circuitry 120 is output to the image processing circuitry 130.

Further, for example, by using the reflected-wave data received from the transmitting and receiving circuitry 110, the signal processing circuitry 120 generates data (Doppler data) obtained by extracting motion information based on the Doppler effect on moving members from each of the sampling points within a scanned region. More specifically, the signal processing circuitry 120 generates the data (the Doppler data) obtained by performing a frequency analysis on the reflected-wave data to acquire velocity information, extracting blood flows, tissues, and contrast-agent echo components subject to the Doppler effect, and extracting moving member information such as an average velocity, a variance value, a power value, and the like from multiple points. In this situation, the moving members may be, for example, blood flows, tissues such as cardiac walls, a contrast agent, and the like. The motion information (blood flow information) obtained by the signal processing circuitry 120 is sent to the image processing circuitry 130 and is displayed on the display 103 in color as an average velocity image, a variance image, a power image, or an image combining any of these images.

Further, as illustrated in FIG. 1, the signal processing circuitry 120 executes an analyzing function 121. In this situation, for example, processing functions executed by the analyzing function 121, which is a constituent element of the signal processing circuitry 120 illustrated in FIG. 1, are recorded in a storage device (e.g., the storage circuitry 150) of the ultrasound diagnosis apparatus 1 in the form of a computer-executable program. The signal processing circuitry 120 is a processor configured to realize functions corresponding to computer programs (hereinafter, "programs"), by reading the programs from the storage device and executing the read programs. In other words, the signal processing circuitry 120 that has read the programs has the functions illustrated within the signal processing circuitry 120 in FIG. 1. The processing functions executed by the analyzing function 121 will be explained later.

The image processing circuitry 130 is configured to generate ultrasound image data from the data generated by the signal processing circuitry 120. From the B-mode data generated by the signal processing circuitry 120, the image processing circuitry 130 is configured to generate B-mode image data in which intensities of the reflected waves are expressed with levels of brightness. Further, from the Doppler data generated by the signal processing circuitry 120, the image processing circuitry 130 is configured to generate Doppler image data expressing the moving member information. The Doppler image data may be velocity image data, variance image data, power image data, or image data combining any of these types of image data.

In this situation, generally speaking, the image processing circuitry 130 converts (by performing a scan convert process) a scanning line signal sequence from an ultrasound scan into a scanning line signal sequence in a video format used by, for example, television and generates display-purpose ultrasound image data. More specifically, the image processing circuitry 130 generates the display-purpose ultrasound image data by performing a coordinate transformation process compliant with the ultrasound scanning mode used by the ultrasound probe 101. Further, as various types of image processing processes other than the scan convert process, the image processing circuitry 130 performs, for example, an image processing process (called a smoothing process) to re-generate an average brightness value image by using a plurality of image frames resulting from the scan convert process and an image processing process (called an edge enhancement process) performed by using a differential filter within an image. Further, the image processing circuitry 130 combines ultrasound image data with additional information (e.g., text information of various parameters, scale graduations, body marks, and/or the like).

In other words, the B-mode data and the Doppler data are each ultrasound image data before the scan convert process is performed. In contrast, the data generated by the image processing circuitry 130 is the display-purpose ultrasound image data after the scan convert process is performed. In this situation, when the signal processing circuitry 120 has generated three-dimensional data (three-dimensional B-mode data and three-dimensional Doppler data), the image processing circuitry 130 generates volume data by performing a coordinate transformation process corresponding to the ultrasound scanning mode used by the ultrasound probe 101. After that, the image processing circuitry 130 generates display-purpose two-dimensional image data by performing various types of rendering processes on the volume data.

The image memory 140 is a memory configured to store therein the display-purpose image data generated by the image processing circuitry 130. Further, the image memory 140 is also capable of storing therein the data generated by the signal processing circuitry 120. The B-mode data and the Doppler data stored in the image memory 140 may be, for example, invoked by the operator after a diagnosis procedure and may serve as display-purpose ultrasound image data after being routed through the image processing circuitry 130.

The storage circuitry 150 is configured to store therein a control computer program (hereinafter "control program") used for performing an ultrasound transmission/reception, image processing processes, and displaying processes, as well as various types of data such as diagnosis information (e.g., patients' IDs, observations of medical doctors, etc.), diagnosis protocols, various types of body marks, and the like. Further, the storage circuitry 150 may also be used for storing therein any of the image data stored in the image memory 140, as necessary. Further, it is also possible to transfer any of the data stored in the storage circuitry 150 to an external apparatus via an interface (not illustrated).

The processing circuitry 160 is configured to control the overall processing of the ultrasound diagnosis apparatus 1. More specifically, the processing circuitry 160 is configured to control processes performed by the transmitting and receiving circuitry 110, the signal processing circuitry 120, and the image processing circuitry 130, on the basis of the various types of setting requests input by the operator via the input device 102 and various types of control programs and various types of data read from the storage circuitry 150. Further, the processing circuitry 160 exercises control so that the display 103 displays the display-purpose ultrasound image data stored in the image memory 140.

Further, as illustrated in FIG. 1, the processing circuitry 160 includes an index value calculating function 161, a determining function 162, a statistic value calculating function 163, and a display controlling function 164. In this situation, for example, processing functions executed by the index value calculating function 161, the determining function 162, the statistic value calculating function 163, and the display controlling function 164, which are constituent elements of the processing circuitry 160 illustrated in FIG. 1, are recorded in a storage device (e.g., the storage circuitry 150) of the ultrasound diagnosis apparatus 1 in the form of computer-executable programs. The processing circuitry 160 is a processor configured to realize the functions corresponding to the programs, by reading the programs from the storage device and executing the read programs. In other words, the processing circuitry 160 that has read the programs has the functions illustrated within the processing circuitry 160 in FIG. 1. The processing functions executed by the index value calculating function 161, the determining function 162, the statistic value calculating function 163, and the display controlling function 164 will be explained later.

The term "processor (or circuit)" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors each realize the functions by reading and executing the programs stored in the storage circuitry 150. It is also acceptable to directly incorporate the programs into the circuits of the processors, instead of storing the programs in the storage circuitry 150. In that situation, the processors each realize the functions by reading and executing the programs incorporated in the circuit thereof. Further, as for the processors according to the first embodiment, each of the processors may be structured as a single circuit. Alternatively, it is also acceptable to realize the functions thereof by structuring a single processor by combining together a plurality of independent circuits. Further, it is also acceptable to integrate the plurality of constituent elements illustrated in each of the drawings into one processor so as to realize the functions thereof.

The ultrasound diagnosis apparatus 1 according to the first embodiment is an apparatus capable of implementing elastography by measuring firmness levels of a tissue in a patient's body and expressing a distribution of the measured firmness levels in an image. More specifically, the ultrasound diagnosis apparatus 1 according to the first embodiment is an apparatus capable of implementing elastography by causing a displacement in the tissue in the patient's body by applying an acoustic radiation force thereto.

In other words, the transmitting and receiving circuitry 110 according to the first embodiment arranges the ultrasound probe 101 to transmit a push pulse that causes the displacement in the tissue in the patient's body on the basis of the acoustic radiation force. Further, the transmitting and receiving circuitry 110 according to the first embodiment further arranges the ultrasound probe 101 to transmit an observation-purpose pulse used for observing the displacement in the tissue in the patient's body caused on the basis of the push pulse. The observation-purpose pulse is transmitted for the purpose of observing, at each of the sampling points in a scanned region, shear velocity of a transverse wave called a shear wave caused by the push pulse. Usually, the observation-purpose pulse is transmitted multiple times (e.g., 100 times) to each of the scanning lines within the scanned region. The transmitting and receiving circuitry 110 generates reflected-wave data from reflected-wave signals of the observation-purpose pulse transmitted with respect to each of the scanning lines within the scanned region. In this situation, the scanned region that is scanned by the observation-purpose pulse corresponds to a region (which may hereinafter be referred to as a "display Region Of Interest (ROI)") in which the firmness levels of the tissue in the patient's body are displayed by using elastography.

Further, in the signal processing circuitry 120, the analyzing function 121 calculates firmness distribution data indicating a distribution of firmness levels in the display ROI, by analyzing the reflected-wave data of the observation-purpose pulse that was transmitted multiple times with respect to each of the scanning lines within the display ROI. More specifically, the analyzing function 121 generates the firmness distribution data of the display ROI, by measuring, at each of the sampling points, the shear velocity of the shear wave caused by the push pulse. In other words, the analyzing function 121 calculates shear velocity values serving as tissue characteristic parameter values, by analyzing a result of the scan performed on the patient P. In this situation, the analyzing function 121 is an example of an analyzing unit. In other words, the analyzing function 121 calculates the tissue characteristic parameter value with respect to each of the plurality of positions within the region of interest, by analyzing the result of the scan performed on the patient.

For example, the analyzing function 121 performs a frequency analysis on the reflected-wave data of the observation-purpose pulse. Accordingly, the analyzing function 121 generates motion information (tissue Doppler data) corresponding to a plurality of temporal phases, at each of the plurality of sampling points on the scanning lines. Further, the analyzing function 121 integrates with respect time the velocity components of the tissue Doppler data corresponding to the plurality of temporal phases and having been obtained at each of the plurality of sampling points on the scanning lines. Accordingly, the analyzing function 121 calculates a displacement corresponding to the plurality of temporal phases at each of the plurality of sampling points on the scanning lines. Subsequently, the analyzing function 121 obtains a time having the largest displacement at each of the sampling points. After that, the analyzing function 121 determines the time having the largest displacement at each of the sampling points, as an arrival time at which the shear wave arrived at the sampling point. Subsequently, the analyzing function 122 calculates the shear velocity value of the shear wave at each of the sampling points, by spatially differentiating the arrival time of the shear wave at each of the sampling points. In this situation, as the arrival time of the shear wave, it is also acceptable to use, for example, a time having the largest amount of change in the displacement at each of the sampling points, instead of the time having the largest displacement at each of the sampling points.

Further, as the firmness distribution data, the analyzing function 121 generates information about the shear velocity value of the shear wave at each of the sampling points within the display ROI. Firmer tissues exhibit higher shear velocity of the shear wave. On the contrary, softer tissues exhibit lower shear velocity of the shear wave. In other words, shear velocity values of the shear wave serve as values indicating levels of firmness (moduli of elasticity) of the tissue. In the example above, the observation-purpose pulse is a transmission pulse for tissue Doppler. Alternatively, for example, it is also acceptable for the analyzing function 121 to calculate the shear velocity value of the shear wave by detecting the shear velocity from a cross-correlation of tissue displacements between adjacently-positioned scanning lines, instead of the calculation based on the time (the arrival time) having the largest displacement at each of the sampling points.

In another example, the analyzing function 121 may calculate a modulus of elasticity (or a Young's modulus or a shearing modulus of elasticity) from the shear velocity and may further generate firmness distribution data by using the calculated modulus of elasticity. It is possible to use the shear velocity, the Young's modulus, and the shearing modulus of elasticity, each as a physical quantity (an index value) indicating a level of firmness of a tissue in a patient's body.

Further, the image processing circuitry 130 generates firmness image data, by assigning, to each of different positions in the display ROI, a picture value corresponding to the shear velocity value at each of the sampling points of the firmness distribution data. The firmness image data generated by the image processing circuitry 130 is displayed by the display 103 as a firmness image, while being superimposed on a B-mode image, for example. In this situation, the firmness image is an image based on the shear velocity values and is an example of an image based on tissue characteristic parameter values.

An example of a configuration of the ultrasound diagnosis apparatus 1 according to the first embodiment has thus been explained. The ultrasound diagnosis apparatus 1 according to the first embodiment configured as described above performs processes described below for the purpose of analyzing a characteristic of a tissue with an excellent level of precision. In other words, the processing circuitry 160 according to the first embodiment executes the index value calculating function 161, the determining function 162, the statistic value calculating function 163, and the display controlling function 164.

In the embodiments described below, an example will be explained in which the "shear velocity values" indicating a level of firmness of a tissue in the patient's body is used as a parameter expressing a characteristic of the tissue (which may be referred to as a "tissue characteristic parameter"). However, possible embodiments are not limited to this example. It is possible to apply an arbitrary tissue characteristic parameter. Other tissue characteristic parameters will be explained later.

The index value calculating function 161 is configured to calculate an index value related to variance among the tissue characteristic parameter values. For example, the index value calculating function 161 calculates an index value for each of a plurality of sub-regions included in a region where a scan was performed. The index value calculating function 161 is an example of an index value calculating unit. In other word the index value calculating function 161 calculates the index value related to the variance among the tissue characteristic parameter values with respect to each of the plurality of sub-regions included in the region of interest.

Figure 2:
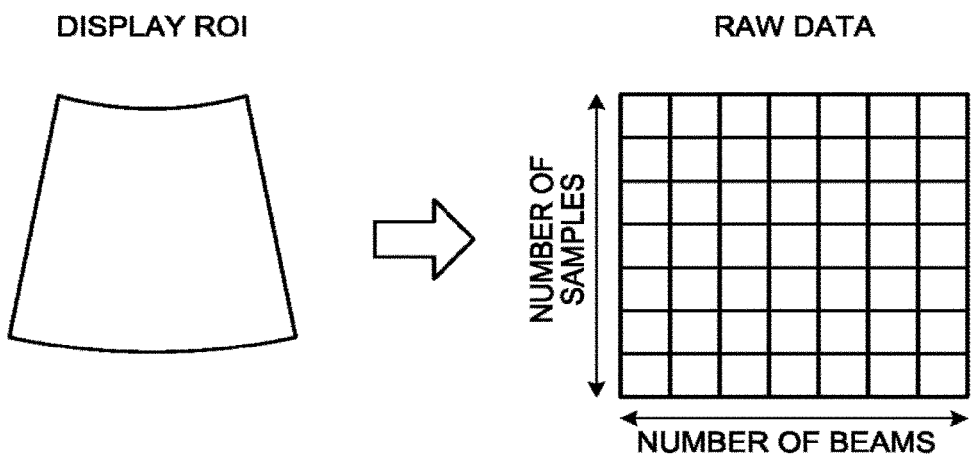
FIG. 2 is a drawing for explaining a process performed by an index value calculating function according to the first embodiment.

FIG. 2 is a drawing for explaining a process performed by the index value calculating function 161 according to the first embodiment. The left section of FIG. 2 illustrates a display ROI expressed in an image by elastography. Further, the right section of FIG. 2 illustrates sampling positions in raw data (prior to the scan conversion) corresponding to the display ROI in the left section of FIG. 2. In the right section of FIG. 2, the horizontal direction (the azimuth direction) corresponds to the number of beams in the display ROI, whereas the vertical direction (the depth direction) corresponds to the number of samples received with each beam.

As illustrated in FIG. 2, the index value calculating function 161 divides a firmness image corresponding to the display ROI into a plurality of sub-regions. More specifically, the index value calculating function 161 divides the azimuth direction of the display ROI into sections at predetermined intervals corresponding to the number of beams and divides the depth direction of the display ROI into sections at predetermined intervals corresponding to the number of samples (the right section of FIG. 2). Each of the regions (hereinafter, "segmented regions") resulting from the dividing performed by the index value calculating function 161 includes a plurality of sampling points. The segmented regions serve as an example of sub-regions.

Further, the index value calculating function 161 calculates a variance among the shear velocity values each of the segmented regions. For example, the index value calculating function 161 calculates, for each of the segmented regions, the variance among the shear velocity values, by using the shear velocity value at each of the plurality of sampling points included in the segmented region.

In this manner, the index value calculating function 161 calculates, for each of the segmented regions, the variance among the shear velocity values, as an index value related to the variance among the tissue characteristic parameter values. The explanation above of the index value calculating function 161 is merely an example. Possible embodiments are not limited to this example. For instance, not only the variance value, the index value calculating function 161 may calculate a standard deviation or a residual sum of squares, as an index value.

Further, in the description above, the example is explained in which the segmented regions obtained by dividing the firm image are used as the sub-regions; however, possible embodiments are not limited to this example. For instance, the sub-regions for each of which the index value is calculated may be regions that each have an arbitrary shape and are positioned in the firmness image in a discrete manner.

The determining function 162 is configured to determine a measurement region on the basis of the index value. For example, the determining function 162 determines the measurement region on the basis of a comparison between the index value of each of the plurality of sub-regions and a threshold value. In the following sections, the measurement region may also be referred to as a "measurement ROI". The determining function 162 is an example of a determining unit. In other words, the determining function 162 determines the measurement region in the region of interest, by performing the analysis while using the tissue characteristic parameter values. Further, the determining function 162 determines the measurement region by comparing the index value of each of the plurality of sub-regions with the threshold value.

Figure 3:
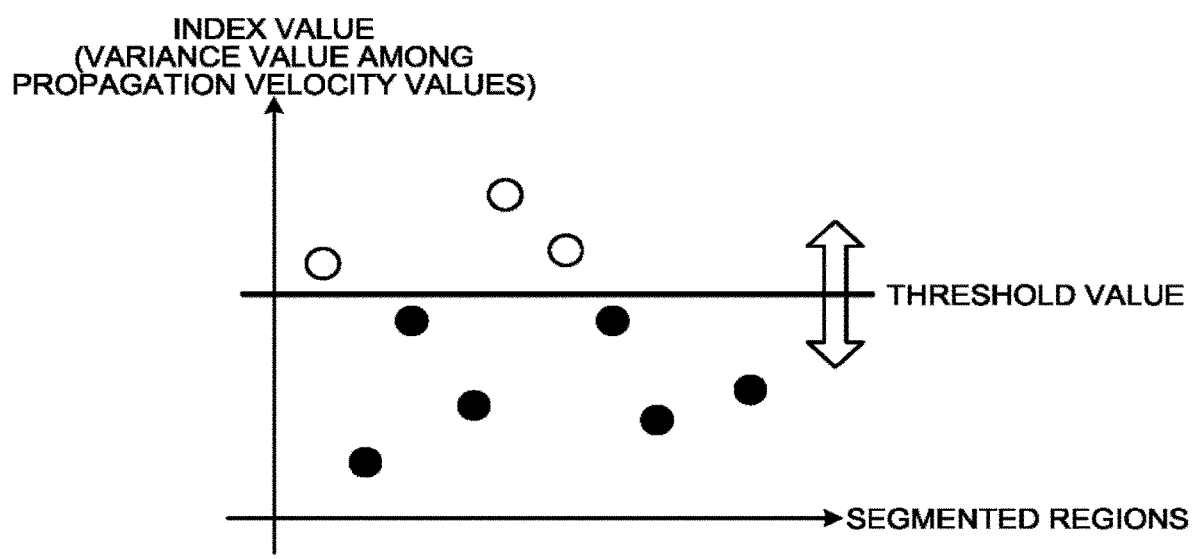
FIG. 3 is a chart for explaining a process performed by a determining function according to the first embodiment.
Figure 4:
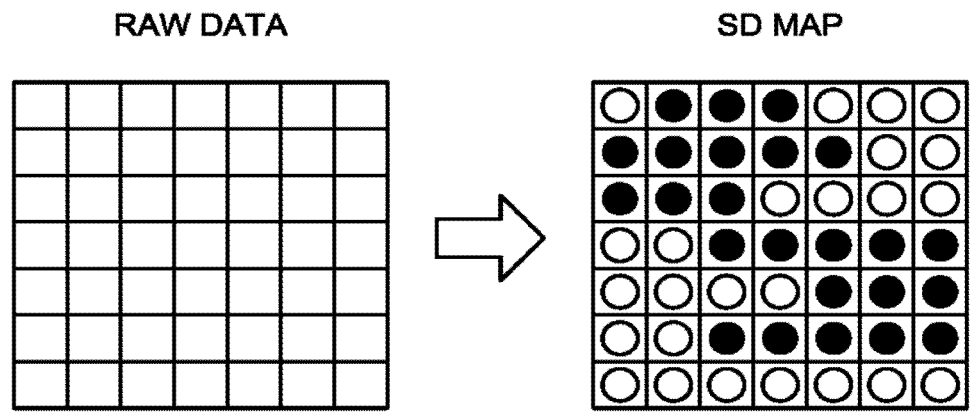
FIG. 4 is a drawing for explaining a process performed by the determining function according to the first embodiment.
Figure 5:
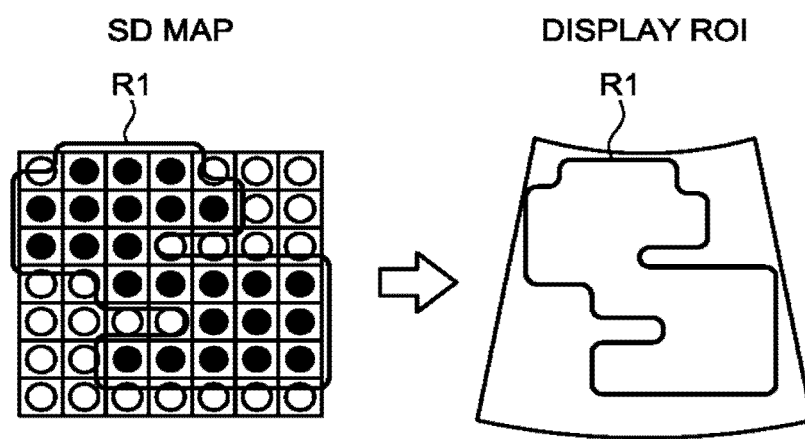
FIG. 5 is another drawing for explaining the process performed by the determining function according to the first embodiment.

FIGS. 3, 4, and 5 are drawings for explaining a process performed by the determining function 162 according to the first embodiment. In FIG. 3, the vertical direction corresponds to the index value (the variance among the shear velocity values), whereas the horizontal direction corresponds to arbitrary segmented regions.

As illustrated in FIG. 3, by comparing the variance among the shear velocity values of each of the segmented regions with the threshold value, the determining function 162 judges whether or not the variance among the shear velocity values is equal to or larger than the threshold value. In the example illustrated in FIG. 3, the segmented regions of which the variance among the shear velocity values is equal to or larger than the threshold value are indicated with white dots, whereas the segmented regions of which the variance among the shear velocity values is smaller than the thresh value are indicated with black dots. In other words, for each of the segmented regions, the determining function 162 judges whether the variance among the shear velocity values of the segmented region is equal to or larger than the threshold value (a white dot) or smaller than the threshold value (a black dot). In this situation, the threshold value used for the comparison with the variance values is a value by which it is possible to determine that the variance among the tissue characteristic parameter values within the segmented region is large. The threshold value is registered by the operator in advance on the basis of reference values from the past. In other words, such a segmented region of which the variance value is equal to or larger than the threshold value is determined to contain noise.

Further, as illustrated in FIG. 4, for example, the determining function 162 generates an SD map on the basis of the result of the comparison between the index value (the variance values) and the threshold value. In the present example, the SD map is information in which the result of the comparison between the variance of each of the segmented regions and the threshold value is indicated in a corresponding position within the raw data. In the example illustrated in FIG. 4, the segmented regions of which the variance is equal to or larger than the threshold value are indicated with "white dots", whereas the segmented regions of which the variance is smaller than the threshold value are indicated with "black dots". In other words, the determining function 162 generates the SD map indicating such a region of which the tissue characteristic parameter value is determined to be noise with a "white dot" and indicating such a region of which the tissue characteristic parameter value is determined not to be noise with a "black dot".

After that, the determining function 162 determines the measurement ROI on the basis of the SD map. For example, the determining function 162 determines at least one measurement ROI from within a region combining together such segmented regions each determined to have small variance. In other words, the determining function 162 rejects (will not adopt) such segmented regions each determined to have large variance and indicated with a "white dot" and further determines the measurement ROI from among such segmented regions each determined to have small variance value and indicated with a "black dot".

In this situation, the determining function 162 determines the measurement ROI according to information (rules) set in advance. For example, the determining function 162 may determine a region having a shape and a size that are set in advance as a measurement ROI. Also, the determining function 162 may determine regions of which the quantity is set in advance, as measurement ROIs.

With reference to FIG. 5, an example will be explained in which the determining function 162 determines a measurement ROI according to the rule where "all the segmented regions each having small variance are determined to form a measurement ROI". In that situation, the determining function 162 determines a region combining together all the segmented regions indicated with the "black dots" in the SD map as a measurement ROI (R1) (the left section of FIG. 5). For example, the determined measurement ROI (R1) is displayed over the display ROI by the display controlling function 164 (explained later) (the right section of FIG. 5).

In this manner, the determining function 162 determines the measurement region on the basis of the variance among the shear velocity values in each of the segmented regions. The above explanation about the determining function 162 is merely an example. Possible embodiments are not limited to this example. For instance, the coordinate system in FIG. 3 as well as the raw data and the SD map in FIGS. 4 and 5 are illustrated for the sake of convenience in the explanation. These pieces of information do not necessarily have to be displayed on the display 103. Further, not only the variance value, the determining function 162 may calculate a standard deviation or a residual sum of squares, as an index value.

Further, although FIG. 4 illustrates the example in which the SD map is generated based on the raw data before the scan conversion is performed, possible embodiments are not limited to this example. For instance, if is also acceptable to generate an SD map based on the image data after the scan conversion (i.e., an image corresponding to the display ROI). Because the sampling positions within the raw data and pixel positions within the image data are kept in correspondence with one another, it is possible to perform the process similarly regardless of whether the data is from before the scan conversion or from after the scan conversion. The scan conversion in this situation does not need to include an interpolation process between the scanning lines.

Further, although FIG. 5 illustrates the example in which the measurement ROI is determined based on the raw data before the scan conversion, possible embodiments are not limited to this example. For instance, it is also acceptable to determine a measurement ROI based on the image data after the scan conversion.

Further, although FIG. 5 illustrates the example in which the single measurement ROI is determined, possible embodiments are not limited to this example. For instance, it is acceptable to determine an arbitrary number of measurement ROIs. Further, besides the rule where "all the segmented regions each having small variance are determined to form a measurement ROI", for example, it is acceptable to determine a measurement ROI by using any of other various rules. For example, it is also acceptable to determine a measurement ROI according to a rule defining an arbitrary shape and an arbitrary size such as "a circular region having the largest diameter (the largest inscribed circle) extracted from within a region combining together all the segmented regions each having small variance, is determined as a measured ROI". Alternatively, for example, it is also acceptable to determine a measurement ROI according to a rule based on a variance value such as "a region that has a predetermined shape and in which an average of the variance values is the smallest is determined as a measurement ROI". Further, the outline of the measurement ROI (R1) in FIG. 5 does not necessarily have to be displayed. An arrangement is also acceptable in which the operator is able to switch between displaying and not displaying of the outline, as appropriate.

When the shape of the measurement ROI is defined by using the rules described above, it is desirable that the shape is defined as a shape to be displayed with the display ROI. The reason is that, for example, a signal sequence from the scanning lines (i.e., the raw data) acquired by performing a sector scan does not match the coordinate system of the display image. In other words, for example, if the shape was defined within the raw data acquired through a sector scan, the defined shape would be changed when the signal is converted into the coordinate system of the display image by the scan conversion. For this reason, when the shape of the measurement ROI is defined, it is desirable that the shape is defined as a shape to be displayed with the display ROI. For example, when a "circular" shape is defined as a shape to be displayed with the display ROI, it is possible to display a "circular" measurement ROI over the display ROI, both before the scan conversion and after the conversion. More specifically, when the process is performed with the image data after the scan conversion, it is possible to set a "circular" measurement ROI, by applying the defined "circular" shape without any modification. Alternatively, when the process is performed with the raw data before the scan conversion, it is possible to set a "circular" measurement ROI, by deforming a "circular" shape (called "reverse deformation") into a shape corresponding to the signal sequence from the scanning lines and applying the deformed shape.

The statistic value calculating function 163 is configured to calculate a statistic value of the tissue characteristic parameter values in the measurement region. For example, the statistic value calculating function 163 calculates an average of the shear velocity values in the measurement ROI. The statistic value calculating function 163 is an example of a statistic value calculating unit. In other words, the statistic value calculating function 163 calculates the statistic value of the tissue characteristic parameter values in the measurement region.

In the example in FIG. 5, the statistic value calculating function 163 calculates an average of the shear velocity values, by using the shear velocity value at each of the plurality of sampling points included in the measurement ROI (R1). When a plurality of measurement ROIs are determined, the statistic value calculating function 163 calculates an average of the shear velocity values for each of the measurement ROIs.

In this manner, the statistic value calculating function 163 calculates the statistic value of the tissue characteristic, parameter values in the measurement region. Although the average value is calculated as the statistic value in the above example, possible embodiments are not limited to this example. Depending on analyses to be performed, it is possible to calculate any arbitrary statistic value such as a median, a variance value, a standard deviation, a residual sum of squares, and/or the like.

The display controlling function 164 is configured to display the measurement region over an image based on the tissue characteristic parameter values. Further, for example, the display controlling function 164 is configured to cause the display 103 to display the statistic value calculated by the statistic value calculating function 163. The display controlling function 164 is an example of a display controlling unit.

For example, as illustrated in FIG. 5, the display controlling function 164 arranges the measurement ROI (R1) to be displayed over the display ROI. Further, the display controlling function 164 arranges the average of the shear velocity values in the measurement ROI (R1) calculated by the statistic value calculating function 163 to be displayed in correspondence with the measurement ROI (R1).

Further, for example, the display controlling function 164 may arrange the sub-regions to be displayed over an image based on the tissue characteristic parameter values. For example, the display controlling function 164 may arrange the plurality of segmented regions indicated in the SD map in FIG. 5 to be displayed over the display ROI.

Figure 6:
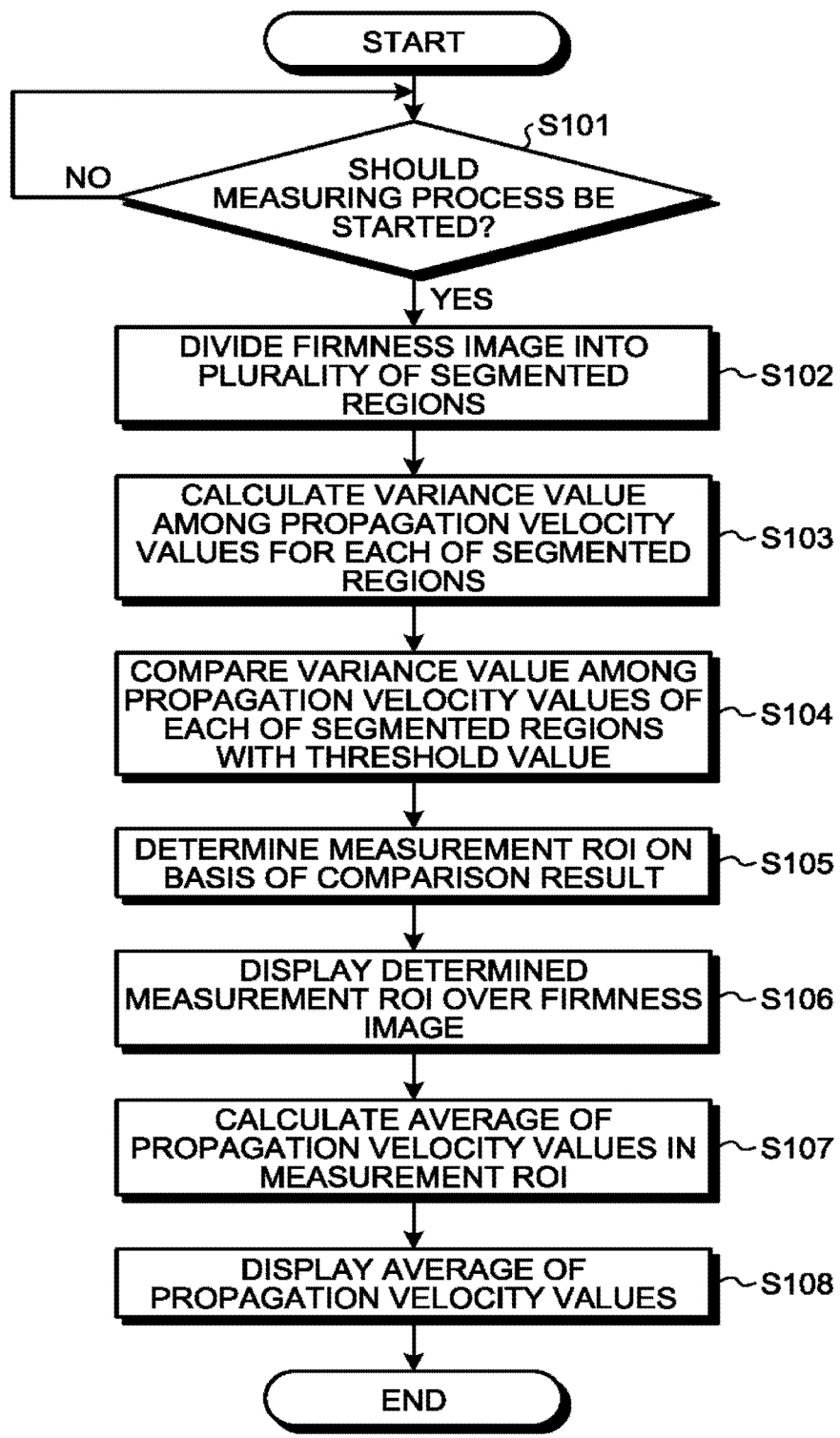
FIG. 6 is a flowchart illustrating a processing procedure performed by the ultrasound diagnosis apparatus according to the first embodiment.

FIG. 6 is a flowchart illustrating a processing procedure performed by the ultrasound diagnosis apparatus 1 according to the first embodiment. The processing procedure illustrated in FIG. 6 is started when, for example, the operator instructs that a measuring process be started while the display 103 is displaying a firmness image subject to the measuring process.

As illustrated in FIG. 6, when an instruction indicating that a measuring process should be started is received (step S101: Yes), the processing circuitry 160 starts the process at step) S102 and thereafter. Unless the processing circuitry 160 receives the instruction indicating that a measuring process should be started (step S101: No), the processing circuitry 160 is in a standby state.

Subsequently, the index value calculating function 161 divides the firmness image into a plurality of segmented regions (step S102). For example, the index value calculating function 161 divides the azimuth direction of the display ROI at predetermined intervals corresponding to the number of beams and divides the depth direction of the display ROI at predetermined intervals corresponding to the number of samples.

Further, the index value calculating function 161 calculates a variance among the shear velocity values for each of the segmented regions (step S103). For example, the index value calculating function 161 calculates, for each of the segmented regions, a variance among the shear velocity values, by using the shear velocity value at each of the plurality of sampling points included in each of the segmented regions.

After that, the determining function 162 compares the variance among the shear velocity values in each of the segmented regions with the threshold value (step S104). For example, the determining function 162 compares, for each of the segmented regions, the variance among the shear velocity values with the threshold value and judges whether or not the variance among the shear velocity values is equal to or larger than the threshold value. After that, the determining function 162 generates an SD map on the basis of results of the comparison between the variances and the threshold values.

Subsequently, the determining function 162 determines a measurement ROI on the basis of the comparison results (step S105). For example, the determining function 162 determines the measurement ROI (R1) on the basis of the SD map. More specifically, the determining function 162 determines either a region having a predetermined shape and a predetermined size or regions of which the quantity is a predetermined value, as one or more measurement ROIs, according to the information (the rule) set in advance.

After that, the display controlling function 164 causes the determined measurement ROI to be displayed over the firmness image (step S106). For example, the display controlling function 164 causes the determined measurement ROI (R1) to be displayed over a display ROI of the firmness image.

Subsequently, the statistic value calculating function 163 calculates an average of the shear velocity values in the measurement ROI (step S107). For example, the statistic value calculating function 163 calculates an average of the shear velocity values, by using the shear velocity value at each of the plurality of sampling points included in the measurement ROI (R1).

After that, the display controlling function 164 causes the average of the shear velocity values to be displayed (step S108). For example, the display controlling function 164 causes the average of the shear velocity values in the measurement ROI (R1) calculated by the statistic value calculating function 163 to be displayed in correspondence with the measurement ROI (R1).

The processing procedure in FIG. 6 explained above is merely an example. Possible embodiments are not limited to this example. For instance, the processing procedure in FIG. 6 does not necessarily have to be performed in the order described above. For example, the process of displaying the measurement ROI (step S106) may be performed at the same time as the process of displaying the average of the shear velocity values (step S108). Further, for example, the process of displaying the measurement ROI (step S106) does not necessarily have to be performed. In other words, it is sufficient as long as the measurement results from the determined measurement ROI are displayed, even without having the measurement ROI displayed.

As explained above, in the ultrasound diagnosis apparatus 1 according to the first embodiment, the analyzing function 121 is configured to calculate the tissue characteristic parameter values by analyzing the result of the scan performed on the patient P. After that, the index value calculating function 161 is configured to calculate the index value related to the variance among the tissue characteristic parameter values. Subsequently, the determining function 162 is configured to determine the measurement region on the basis of the index value. The statistic value calculating function 163 is configured to calculate the statistic value of the tissue characteristic parameter values in the measurement region. With these arrangements, the ultrasound diagnosis apparatus 1 makes it possible to analyze the tissue characteristic with an excellent level of precision.

Figure 7:
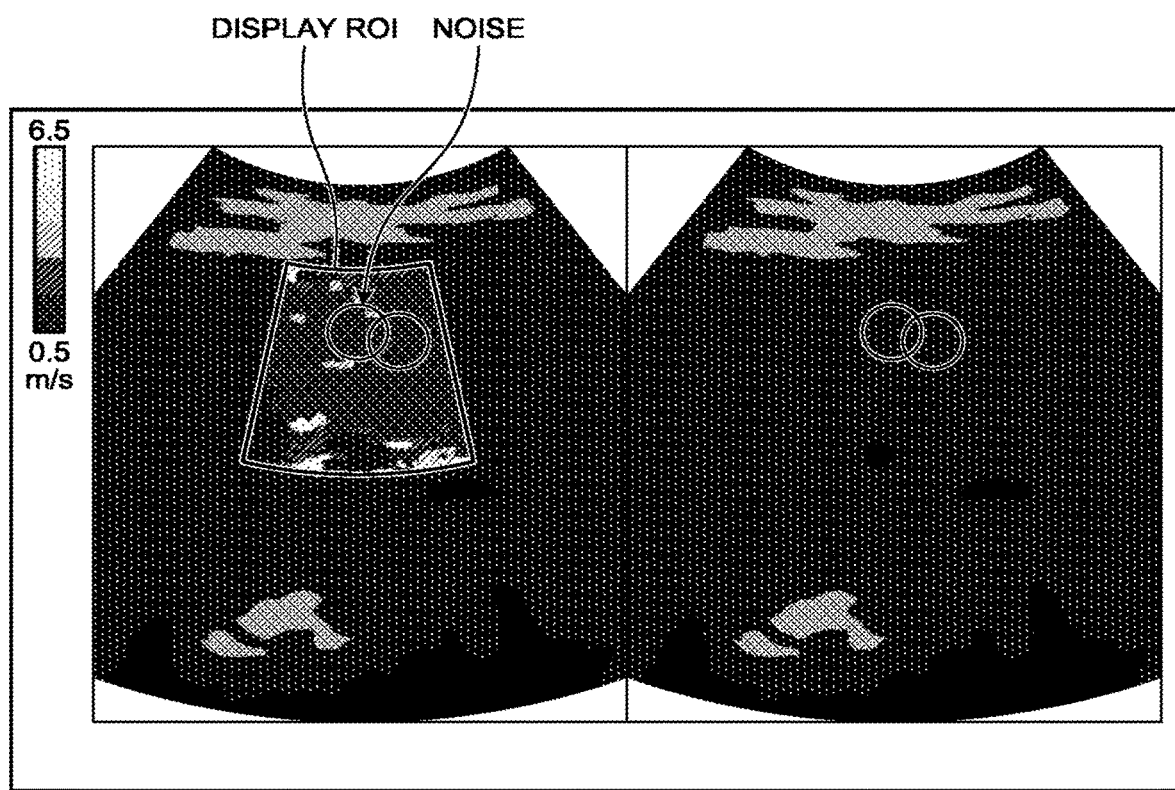
FIG. 7 is a drawing for explaining advantageous effects achieved by the ultrasound diagnosis apparatus according to the first embodiment.

FIG. 7 is a drawing for explaining advantageous effects achieved by the ultrasound diagnosis apparatus 1 according to the first embodiment. FIG. 7 illustrates an example in which two circular measurement ROIs are set in a firmness image corresponding to a display ROI within a B-mode image.

In the display ROI in FIG. 7, although the firmness image having substantially uniform firmness levels (shear velocity) is displayed, there are a number of locations where the levels of firmness are partially different. Such regions represent, for example, noise caused by impacts from nearby structures or blood vessels. It is considered that such regions do not indicate the actual firmness levels of the tissue (a tissue characteristic). In this situation, when measurement ROIs are manually designated, there is a possibility that the measurement ROIs may contain noise. In the example in FIG. 7, the measurement ROI on the left-hand side contains noise. For this reason, if a measuring process were performed by using the measurement ROI positioned on the left, results of the measuring process (e.g., an average of firmness levels) would also contain noise.

To cope with this situation, the ultrasound diagnosis apparatus 1 according to the first embodiment is configured, when performing a measuring process in a firmness image, to calculate a variance among shear velocity values, serving as tissue characteristic parameter values indicating levels of firmness, with respect to each of the sub-regions and to further set measurement ROIs each in a region having small variance among the shear velocity values. With this configuration, for example, the ultrasound diagnosis apparatus 1 is able to set regions containing no noise as the measurement ROIs, as indicated by the measurement ROIs illustrated in the right section of FIG. 7. The ultrasound diagnosis apparatus 1 thus makes it possible to analyze the tissue characteristic with an excellent level of precision.

Further, when performing a measuring process by using a firmness image based on the shear velocity values of the shear wave, the ultrasound diagnosis apparatus 1 according to the first embodiment determines one or more measurement ROIs by directly evaluating the shear velocity values themselves, which are subject to the measuring process. With this configuration, the ultrasound diagnosis apparatus 1 is able to determine, as the measurement ROIs, stable regions that each have small variance among the tissue characteristic parameter values, which are subject to the measuring process.

Further, the ultrasound diagnosis apparatus 1 according to the first embodiment automatically determines the measurement ROIs by performing the process described above. Consequently, the ultrasound diagnosis apparatus 1 is able to set the appropriate measurement ROIs with a simple operation, without requiring the operator to perform complicated operations.

Second Embodiment

In the first embodiment, the example is explained in which the ultrasound diagnosis apparatus 1 automatically determines the measurement ROIs. However, possible embodiments are not limited to this example. For instance, another arrangement is also acceptable in which the ultrasound diagnosis apparatus 1 is configured to determine one or more measurement candidate regions (which may be referred to as "measurement candidate ROIs") serving as candidates for a measurement ROI and to further determine a region selected by the operator froze among the determined measurement candidate ROIs as a measurement ROI.

The ultrasound diagnosis apparatus 1 according to the second embodiment has a similar configuration to that of the ultrasound diagnosis apparatus 1 illustrated in FIG. 1 where a part of the process performed by the determining function 162 is different. The second embodiment therefore will be explained by placing a focus on differences from the first embodiment. Explanations of some of the configurations having the same functions as those explained in the first embodiment will be omitted.

The determining function 162 is configured to determine measurement candidate ROIs on the basis of a comparison between index values and a threshold value. For example, the determining function 162 determines at least one measurement candidate region on the basis of a comparison between an index value of each of the plurality of sub-regions and the threshold value. After that, the determining function 162 determines a measurement region from among said at least one measurement candidate region.

For example, the determining function 162 determines a measurement ROI on the basis of an SD map. For example, the determining function 162 determines at least one measurement candidate ROI from within a region combining together such segmented regions each determined to nave small variance.

In this situation, the determining function 162 determines the measurement candidate ROI according to information (a rule) set in advance. For example, the determining function 162 determines a measurement candidate ROI having a shape and a size set in advance. Also, the determining function 162 determines one or more measurement candidate ROIs of which the quantity is set in advance.

Figure 8A:
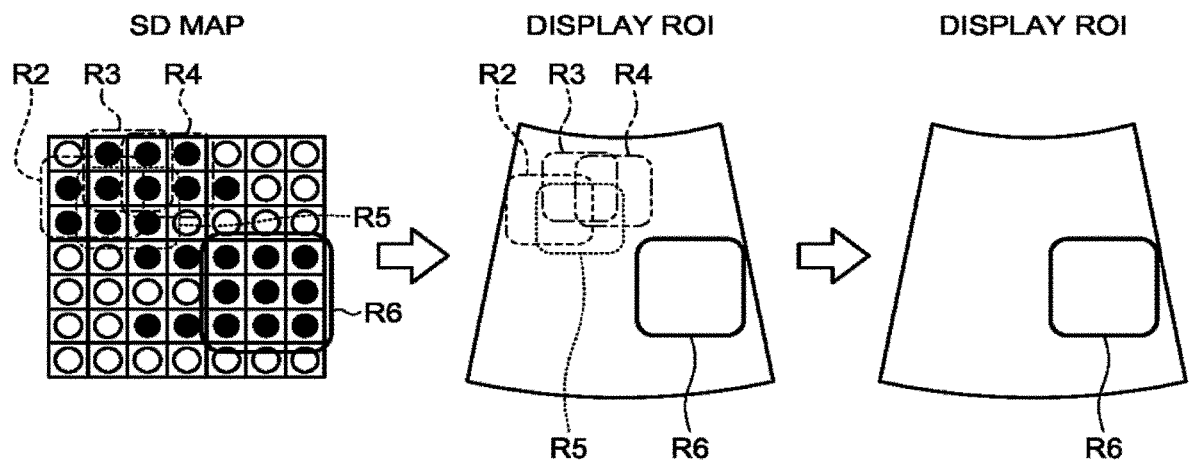
FIGS. 8A and 8B are drawings for explaining a process performed by a determining function according to a second embodiment.
Figure 8B:
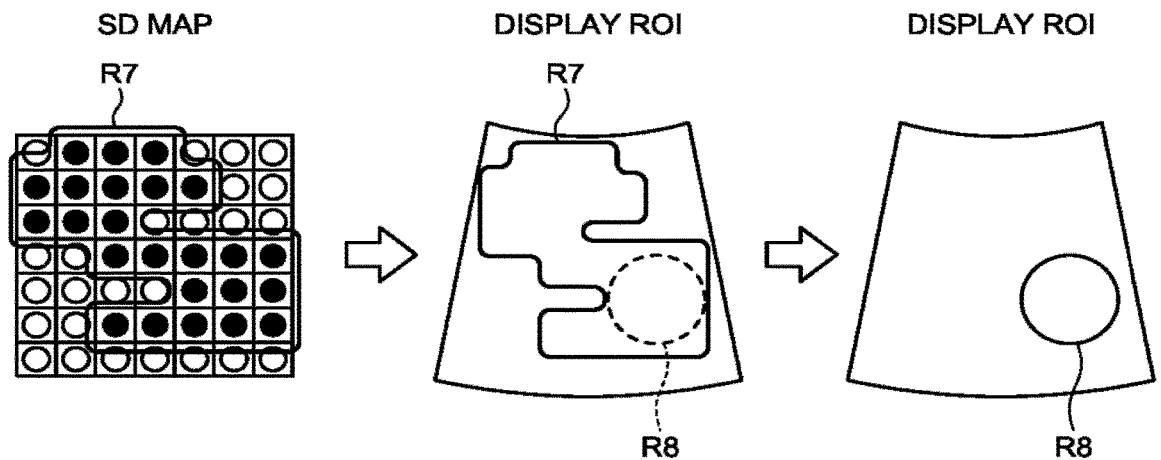

FIGS. 8A and 8B are drawings for explaining a process performed by the determining function 162 according to the second embodiment. For example, the determining function 162 determines one or more measurement candidate ROIs according to the rules illustrated in FIGS. 8A and 8B.

The example in FIG. 8A illustrates an example in which the determining function 162 determines measurement candidate ROIs and further determines a measurement ROI from among the measurement candidate ROIs according to the rule where "a square region made up of segmented regions each having small variance that are arranged in a 2 by 2 or larger formation is selected as a measurement candidate ROI". In this situation, from the region combining together the segmented regions indicated with the "black dots" in the SD map, the determining function 162 extracts square regions each made up of segmented regions arranged in a 2 by 2 or larger formation and determines the extracted regions as measurement candidate ROIs. In the left section of FIG. 8A, the determining function 162 determines a measurement candidate ROI (R2), a measurement candidate ROI (R3), a measurement candidate ROI (R4), a measurement candidate ROI (R5), and a measurement candidate ROI (R6). The determined measurement candidate ROIs are displayed over the display ROI by the display controlling function 164 (the middle section of FIG. 8A) After that, the determining function 162 receives, from the operator, an operation to select a measurement ROI from among the determined measurement candidate ROIs. For example, when having received from the operator an operation to select the measurement candidate ROI (R6) as a measurement ROI, the determining function 162 determines the measurement candidate ROI (R6) to be a measurement ROI (R6). In that situation, for example, the measurement candidate ROIs other than the measurement ROI (R6) are brought into a non-display state, so that only the measurement ROI (R6) is displayed (the right section of FIG. 8A).

The example in FIG. 8B illustrates an example in which, according to the rule where "all the segmented regions each having small variance are determined to form a measurement candidate ROI", the determining function 162 determines a measurement candidate ROI and further determines a measurement ROI having an arbitrary shape within the measurement candidate ROI. In that situation, the determining function 162 determines a region combining together all the segmented regions indicated with the "black dots" in the SD map as a measurement candidate ROI (R7) (the left section of FIG. 8B). For example, the determined measurement candidate ROI (R7) is displayed over the display ROI by the display controlling function 164 (the middle section of FIG. 8B). After that, from the operator, the determining function 162 receives an operation to designate a measurement ROI having an arbitrary shape from within the area of the measurement candidate ROI (R7). For example, the operator performs an operation of designating a circular region (R8) as the measurement ROI, from within the area indicated with the outline of the measurement candidate ROI (R7) displayed over the display ROI (the middle section of FIG. 8B). When having received the operation, the determining function 162 determines the region (R8) as a measurement ROI (R8). In that situation, for example, the measurement candidate ROI (R7) is brought into a non-display state, so that only the measurement ROI (R8) is displayed (the right section of FIG. 8B).

As explained above, the determining function 162 determines the one or more measurement candidate regions on the basis of the variance value among the shear velocity values in each of the segmented regions and further determines the measurement region from among or from within the one or more determined measurement candidate regions. The above description of the determining function 162 is merely an example. Possible embodiments are not limited to this example. For instance, although the example is explained above in which the plurality of measurement candidates ROIs are determined, possible embodiments are not limited to this example. For instance, a single measurement candidate ROI may be determined.

Further, for example, FIG. 8A illustrates the example in which the operator selects the measurement ROI from among the plurality of measurement candidates ROIs. However, possible embodiments are not limited to this example. For instance, the determining function 162 may automatically select a measurement ROI from among the plurality of measurement candidate ROIs. For example, the determining function 162 may determine a measurement ROI according to the rule where "the largest region of a plurality of measurement candidate ROIs is determined as a measurement ROI". In that situation, the determining function 162 determines the measurement candidate ROI (R6) as a measurement ROI (R6). In another example, the determining function 162 may determine a measurement ROI according to the rule where "a region having the smallest variance value among a plurality of measurement candidates ROIs is determined as a measurement ROI". In that situation, the determining function 162 calculates a variance value of each of the measurement candidates ROI and determines one of the measurement candidate ROIs having the smallest variance value as a measurement ROI.

Figure 9:
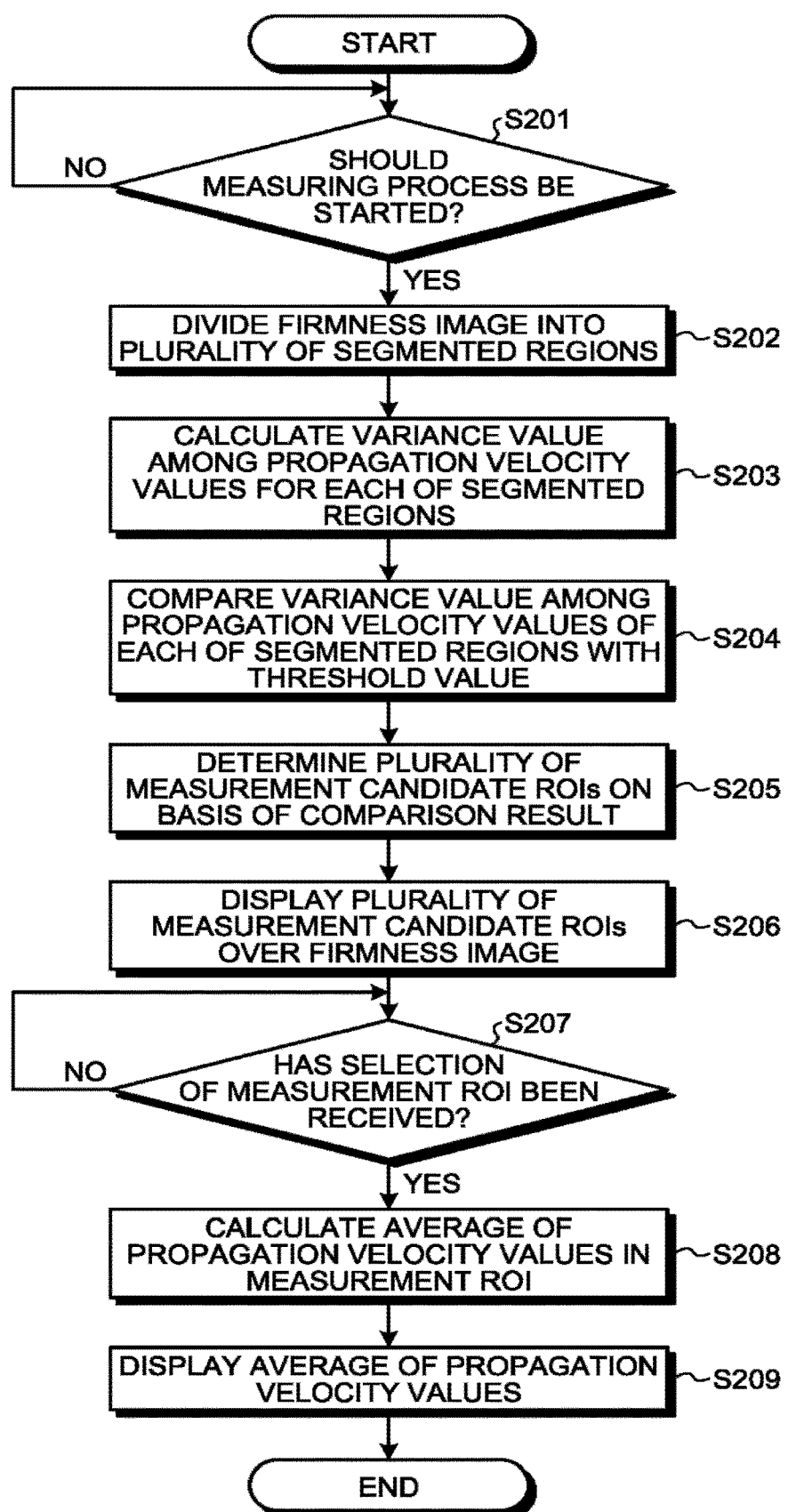
FIG. 9 is a flowchart illustrating a processing procedure performed by an ultrasound diagnosis apparatus according to the second embodiment.

FIG. 9 is a flowchart illustrating a processing procedure performed by the ultrasound diagnosis apparatus according to the second embodiment. For example, the processing procedure in FIG. 9 is started when the operator instructs that a measuring process should be started while a firmness image subject to the measuring process is being displayed on the display 103. Of the processing procedure in FIG. 9, because the processes at steps S201 through S204 are the same as the processes at steps S101 through S104 in FIG. 6, explanations thereof will be omitted.

As illustrated in FIG. 6, the determining function 162 determines a plurality of measurement candidate ROIs on the basis of the results of the comparison (step S205). For example, the determining function 162 determines a plurality of measurement candidate ROIs on the basis of the SD map. More specifically, according to information (a rule) set in advance, the determining function 162 determines either regions each having a predetermined shape and a predetermined size or regions of which the quantity is a predetermined value, as the measurement candidates ROIs.

After that, the display controlling function 164 causes the determined plurality of measurement candidate ROIs to be displayed over the firmness image (step S206). For example, the display controlling function 164 causes the determined plurality of measurement candidates ROIs to be displayed over a display ROI.

Subsequently, the determining function 162 receives a selection of a measurement ROI (step S207). For example, the determining function 162 receives, from the operator, an operation to select the measurement ROI from among the plurality of measurement candidate ROIs displayed over the display ROI. When having received the operation (step 207: Yes), the determining function 162 determines the measurement candidate ROI selected by the operation as a measurement ROI. Unless the determining function 162 receives an operation to select a measurement ROI (step S207: No), the determining function 162 is in a standby state.

Further, the statistic value calculating function 163 calculates an average of the shear velocity values in the measurement ROI (step S208) and causes the calculated average of the shear velocity values to be displayed (step S209). Because the processes at steps S208 and S209 are the same as the processes at steps S107 and S108 in FIG. 6, explanations thereof will be omitted.

The processing procedure in FIG. 9 explained above is merely an example. Possible embodiments are not limited to this example. For instance, although the example is explained above in which the statistic value (the average of the shear velocity values) is calculated only with respect to the determined measurement ROI, possible embodiments are not limited to this example. For instance, a statistic value may be calculated for each of all the measurement candidate ROIs. With this arrangement, for example, the operator is able to select a measurement ROI from among the measurement candidate ROIs, by referring to the statistic value of each of the measurement candidate ROIs.

As explained above, in the ultrasound diagnosis apparatus 1 according to the second embodiment, the analyzing function 121 is configured to calculate the tissue characteristic parameter values by analyzing the result of the scan performed on the patient P. After that, the index value calculating function 161 is configured to calculate the index value related to the variance among the tissue characteristic parameter values. Subsequently, the determining function 162 is configured to determining the measurement candidate regions on the basis of the index values. After that, the display controlling function 164 is configured to cause the measurement candidate regions to be displayed over the image based on the tissue characteristic parameter values. With these arrangements, the ultrasound diagnosis apparatus 1 presents the plurality of measurement candidate ROIs containing no noise to the operator. The ultrasound diagnosis apparatus 1 is thus able to analyze the tissue characteristic with an excellent level of precision, realized with a simple operation.

Other Embodiments

It is possible to carry out the present disclosure in other various modes besides the embodiments described above.

Changing the Size of the Segmented Regions

For example, in the embodiments described above, the example is explained in which the segmented regions having the size set in advance are used. However, possible embodiments are not limited to is example. For instance, the operator is able to arbitrarily change the size of the segmented regions.

Figure 10:
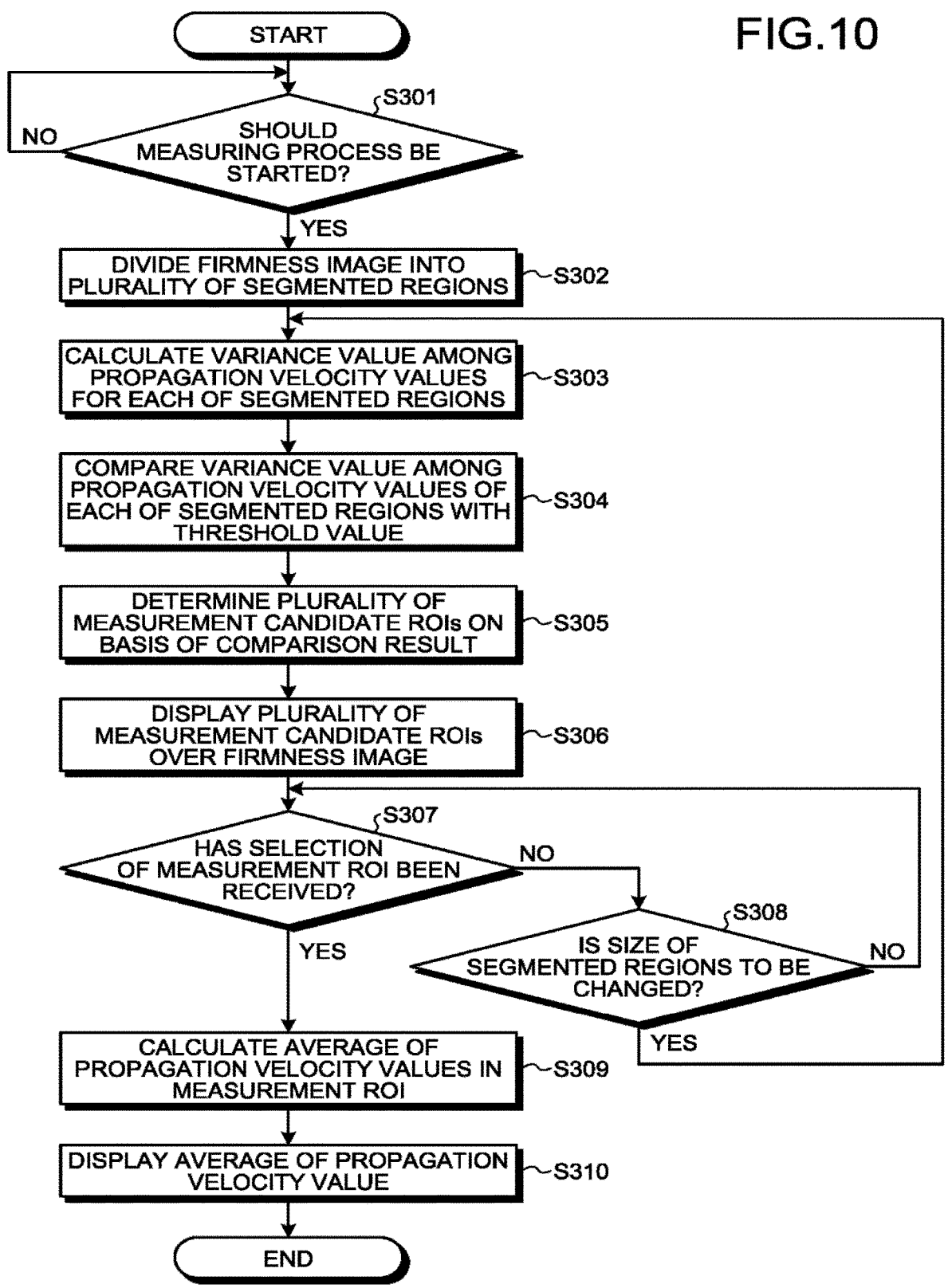
FIG. 10 is a flowchart illustrating a processing procedure performed by an ultrasound diagnosis apparatus according to another embodiment.

FIG. 10 is a flowchart illustrating a processing procedure performed by the ultrasound diagnosis apparatus 1 according to another embodiment. Of the processing procedure illustrated in FIG. 10, because the processes at steps S301 through S307 are the same as the processes at steps S201 through S207 in FIG. 9, explanations thereof will be omitted.

As illustrated in FIG. 10, unless the processing circuitry 160 receives a selection of a measurement ROI (step S307: No), the processing circuitry 160 is in a standby state. In that situation, when having received, from the operator, an instruction indicating that the size of the segmented regions should be changed (step S308: Yes), the input device 102 outputs the received instruction to the processing circuitry 160. After that, when having received the instruction of the operator from the input device 102, the processing circuitry 160 proceeds to the process at step S303. In other words, the index value calculating function 161 changes the size of the segmented regions in response to the instruction from the operator and further re-calculates a variance value among the shear velocity values by using the segmented regions having the post-change size.

Figure 11:
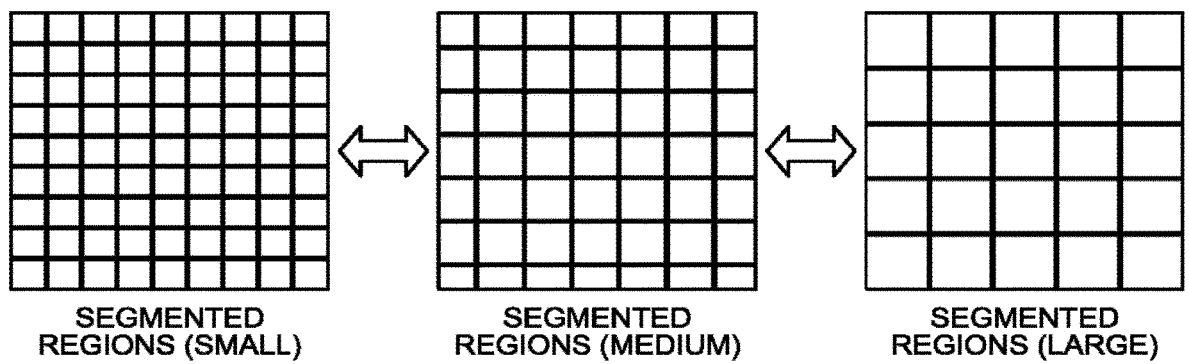
FIG. 11 is a drawing for explaining a process performed by an index value calculating function according to said another embodiment.

FIG. 11 is a drawing for explaining a process performed by the index value calculating function 161 according to said another embodiment. As illustrated in FIG. 11, the index value calculating function 161 changes the size of the segmented regions on three levels, in accordance with an instruction from the operator. More specifically, the size of the segmented regions is set in advance on one of the three levels, namely segmented regions (small), segmented regions (medium), and segmented regions (large). It is desirable to set the size of the segmented regions so that the display ROI is divisible (so that there is no remainder). Further, the size of the segmented regions is kept in association with an operation performed on a dial switch. For example, by operating the dial switch, the operator is able to change the size of the segmented regions. Further, the index value calculating function 161 sets the size to one selected from among the segmented regions (small), the segmented regions (medium), and the segmented regions (large) in response to the instruction from the operator. Subsequently, by using the segmented regions having the set size, the index value calculating function 161 re-calculates a variance value among the shear velocity values (step S303). After that, the processes at step S304 and thereafter are sequentially performed.

On the contrary, when the size of the segmented regions is not to be changed (step S308: No), the processing circuitry 160 proceeds to the process at step S307. In other words, unless the processing circuitry 160 receives either a selection of a measurement ROI or a change made to the size of the segmented regions, the processing circuitry 160 is in a standby state. Because the processes at steps S309 and S310 are the same as the processes at steps S208 and S209 in FIG. 9, explanations thereof will be omitted.

As a result, the ultrasound diagnosis apparatus 1 is able to set the segmented regions having the size arbitrarily selected by the operator. Accordingly, the operator is able to change the size of the segmented regions to an arbitrary size in accordance with a desired size of the measurement ROI, for example, by setting the size of the segmented regions to 10 mm (or a divisor of 10 mm) when the desired size of the measurement ROI is 10 mm.

Changing the Threshold Value for the Variance

For example, in the embodiments described above, the example is explained in which the threshold value set in advance is used. However, possible embodiments are not limited to this example. For instance, the operator is able to arbitrarily change the threshold value.

Figure 12:
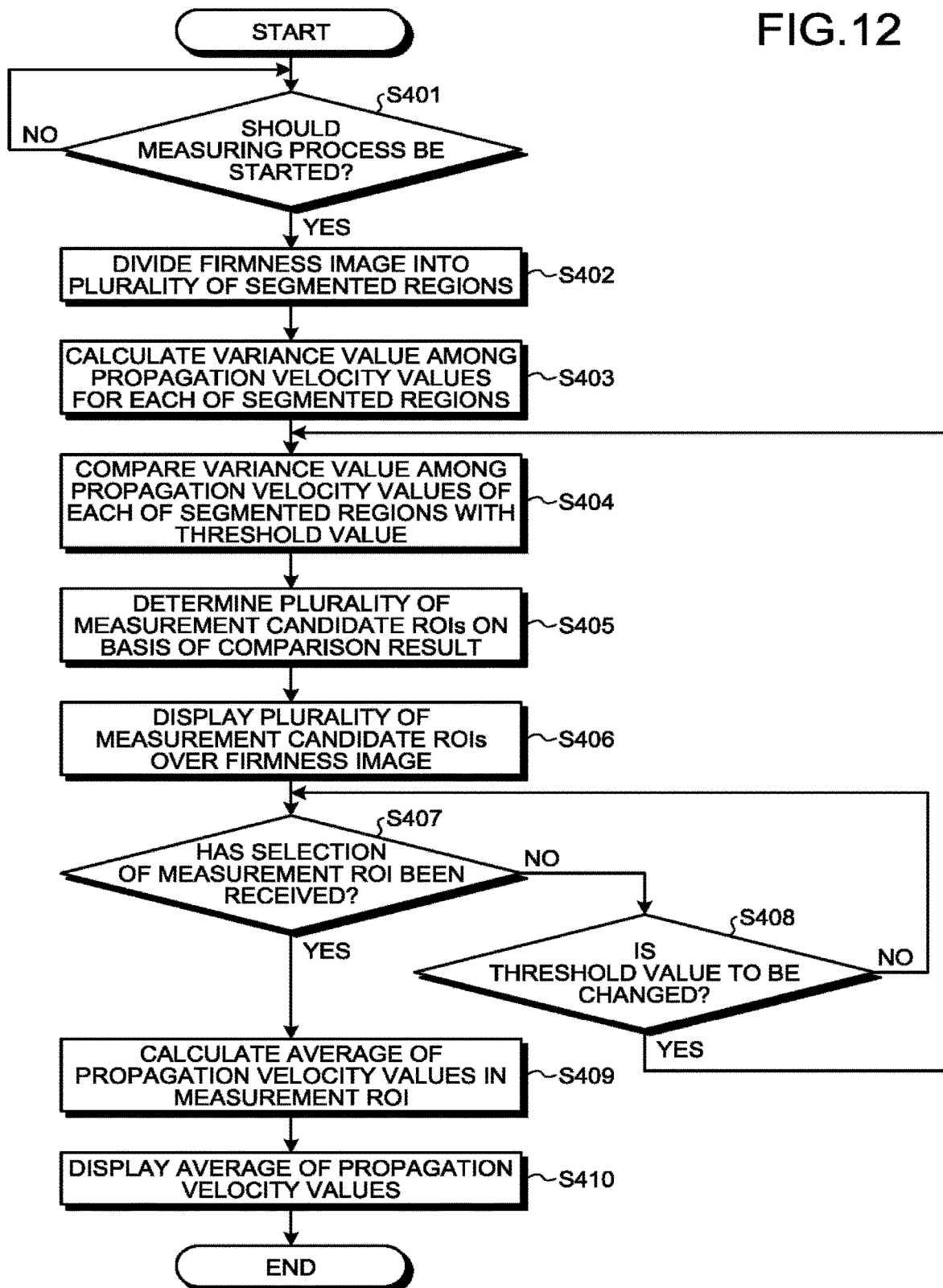
FIG. 12 is a flowchart illustrating a processing procedure performed by the ultrasound diagnosis apparatus according to yet another embodiment.

FIG. 12 is a flowchart illustrating a processing procedure performed by the ultrasound diagnosis apparatus 1 according to yet another embodiment. Of the processing procedure illustrated in FIG. 12, because the processes at steps S401 through S407 are the same as the processes at steps S201 through S207 in FIG. 9, explanations thereof will be omitted.

As illustrated in FIG. 12, unless the processing circuitry 160 receives a selection of a measurement ROI (step S407: No), the processing circuitry 160 is in a standby state. In that situation, when having received an operation to change the threshold value from the operator (step S408: Yes), the input device 102 outputs the received instruction to the processing circuitry 160. After that, when having received the instruction of the operator from the input device 102, the processing circuitry 160 proceeds to the process at step S404. In other words, the determining function 162 changes the threshold value in response to the operation from the operator and further compares the variance among the shear velocity values in each of the segmented regions, by using the post-change threshold value (step S404).

Figure 13:
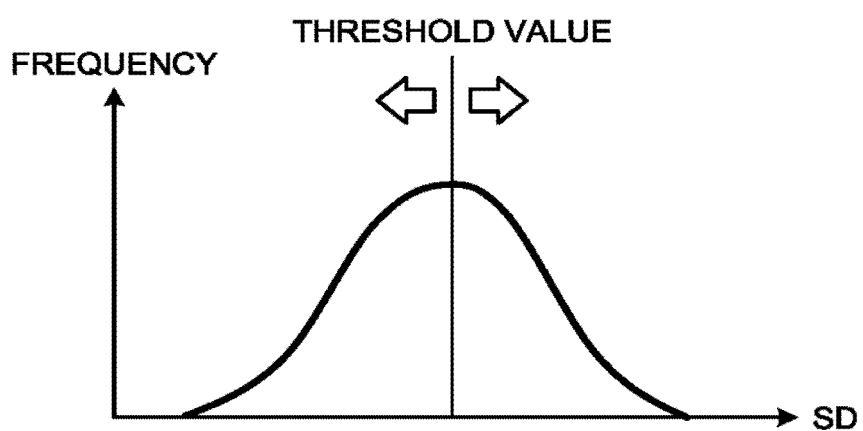
FIG. 13 is a chart for explaining a process performed by a determining function according to said yet another embodiment.

FIG. 13 is a chart for explaining a process performed by the determining function 162 according to said yet another embodiment. In the example in FIG. 13, a histogram is displayed for the purpose of receiving an operation to change the threshold value from the operator. In the histogram, the horizontal direction corresponds to a standard deviation (SD) (a variance value), whereas the vertical direction corresponds to frequency (the number of segmented regions). In the histogram, the threshold value is expressed as a line in the vertical direction. In FIG. 13, positioned on the right-hand side of the line is a region determined to have large variance, whereas positioned on the left-hand side of the line is a region determined to have small variance.

In this situation, by operating the input device 102 such as a mouse, the operator moves the position of the line indicating the threshold value either to the left or to the right. When having received the operation to change the position of the line, the determining function 162 changes the threshold value to a value corresponding to the position of the line designated by the received operation. After that, the determining function 162 compares the post-change threshold value with the variance value among the shear velocity values of each of the segmented regions (step S404). Subsequently, the processes at step S405 and thereafter are sequentially performed.

On the contrary, when the threshold value is not to be changed (step S408: No), the processing circuitry 160 proceeds to the process at step S407. In other words, unless the processing circuitry 160 receives either a selection of a measurement ROI or a change made to the threshold value, the processing circuitry 160 is in a standby state. Because the processes at steps S409 and S410 are the same as the processes at steps S208 and S209 in FIG. 9, explanations thereof will be omitted.

With these arrangements, the ultrasound diagnosis apparatus 1 is able to change the threshold value to a value arbitrarily determined by the operator. Consequently, for example, the operator is able to set an appropriate threshold value in accordance with the patient's site subject to the measuring process. The process of changing the threshold value described above is merely an example. Possible embodiments are not limited to this example. For instance, the determining function 162 may change the threshold value in accordance with the patient's site subject to the measuring process. For example, an arrangement is acceptable in which an appropriate threshold value is registered in advance for each of various sites, so that the determining function 162 determines a threshold value by reading a threshold value corresponding to the site designated by the operator.

An Application of a Machine Learning Scheme

In the embodiments described above, the example is explained in which the measurement ROI (or the measurement candidate ROI) is determined by using the index values related to the variance among the tissue characteristic parameter values. However, possible embodiments are not limited to this example. For instance, the ultrasound diagnosis apparatus 1 is also capable of determining the measurement ROI (or the measurement candidate ROI) by applying a machine learning scheme to information about a distribution of the tissue characteristic parameter values.

More specifically, the index value calculating function 161 obtains distribution information of the tissue characteristic parameter values with respect to each of the plurality of sub-regions included in the region of interest. Further, the index value calculating function 161 calculates an index value indicating a degree of stability of the tissue characteristic parameter values of each of the sub-regions, by using the distribution information of the tissue characteristic parameter values as an input to a trained machine learning scheme. Further, by comparing the index value of each of the plurality of sub-regions with a threshold value, the determining function 162 determines a measurement region (or a measurement candidate region).

Figure 14:
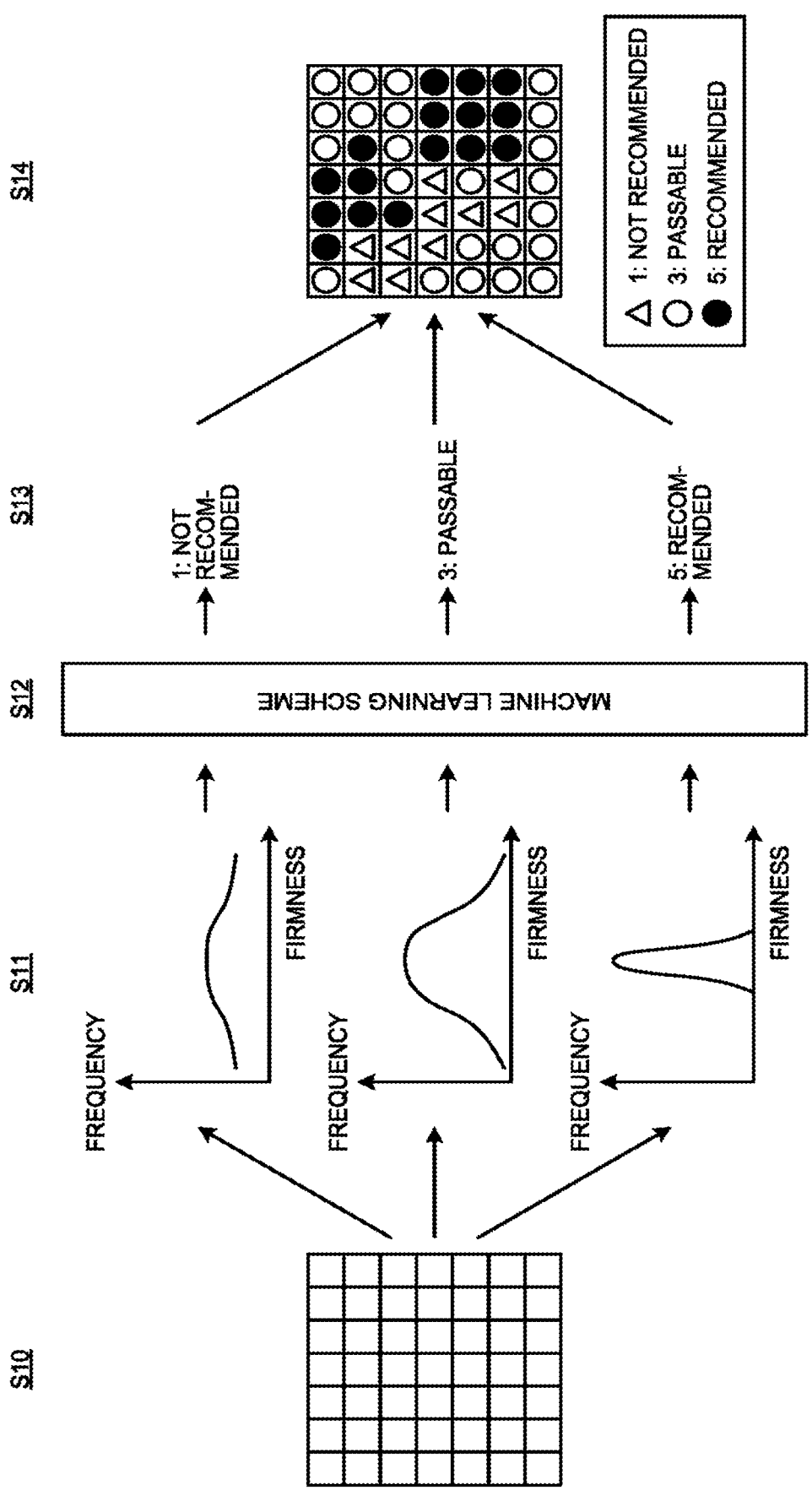
FIG. 14 is a drawing for explaining a process performed by an ultrasound diagnosis apparatus according to yet another embodiment.

FIG. 14 is a drawing for explaining a process performed by the ultrasound diagnosis apparatus 1 according to yet another embodiment. FIG. 14 illustrates details of the process performed by the ultrasound diagnosis apparatus 1 according to said yet another embodiment sequentially in the order of steps S10 through S14.

As illustrated in FIG. 14, at step S10, the index value calculating function 161 divides a firmness image corresponding to a display ROI into a plurality of sub-regions (segmented regions). Because this process performed by the index value calculating function 161 is the same as the process performed by the index value calculating function 161 explained with reference to FIG. 2, explanation thereof will be omitted.

At step S11, the index value calculating function 161 generates a histogram for each of the segmented regions. For example, the index value calculating function 161 generates the histogram by plotting levels of firmness of the pixels included in each of the segmented regions. More specifically, in the histograms, the vertical axis corresponds to frequency (the number of pixels), whereas the horizontal axis corresponds to the level of firmness (the shear velocity value). Although the histograms in the three patterns are illustrated in the present example, possible histograms are not limited to those in this example. Further, the histograms serve as an example of the distribution information of the tissue characteristic parameter values.

At step S12, the index value calculating function 161 uses the histograms of the segmented regions as an input to the machine learning scheme. The machine learning scheme has learned in advance a correspondence relationship between various shapes of histograms and stability scores (degrees of stability) corresponding to the histogram shapes. In this situation, each of the stability scores is an index value indicating how stable the levels of firmness in the segmented region are (how constant the levels of firmness are).

For example, as illustrated in the chart in the bottom section of step S11, an ideal segmented region containing no noise exhibits a histogram having a protruding shape, because the levels of firmness of the pixels are close to a certain value (the variance is small). In that situation, a larger value is given as the stability score. In contrast, as illustrated in the charts in the middle and the top sections of step S11, the larger the noise in the segmented region is, the flatter the shape of the histogram becomes, because the levels of firmness of the pixels in the segmented region do not exhibit a constant value (the variance is large). Thus, the flatter the histogram is, the smaller value is given as the stability score.

In other words, when the index value calculating function 161 inputs the histograms of the segmented regions to the machine learning scheme, the machine learning scheme outputs stability scores corresponding to the shapes of the input histograms. In the present example, the machine learning scheme is created by the operator (or a designer of the ultrasound diagnosis apparatus 1) in advance.

At step S13, the index value calculating function 161 calculates a stability score of each of the segmented regions. For example, the index value calculating function 161 assigns the stability scores output by the machine learning scheme to the segmented regions. In other words, the index value calculating function 161 assigns the stability score "5: Recommended" to any of the segmented regions exhibiting a histogram having a protruding shape. Further, the index value calculating function 161 assigns the stability score "1: Not Recommended" to any of the segmented regions exhibiting a histogram having a flat shape. Further, the index value calculating function 161 assigns the stability score "3: Passable" to any of the segmented regions exhibiting a histogram having a shape somewhere in the middle of a protruding shape and a flat shape. In this manner, the index value calculating function 161 assigns a stability score to each of the segmented regions included in the display ROI. The stability scores serve as an example of the degree of stability.

At step S14, the determining function 162 generates a stability score map. For example, the determining function 162 generates the stability score map by using the stability scores of the segmented regions calculated by the index value calculating function 161. In the present example, the stability score map is information obtained by expressing each of the stability scores of the segmented regions in a corresponding position within the display ROI. In the example in FIG. 14, such segmented regions that each have the stability score "5: Recommended" are indicated with "black dots", while such segmented regions that each have the stability score "3: Passable" are indicated with "white dots", and such segmented regions that each have the stability score "1: Not Recommended" are indicated with "triangles".

For example, the determining function 162 determines a measurement ROI on the basis of the stability score map. In one example, the determining function 162 determines at least one measurement ROI having an arbitrary shape from within a region combining together a plurality of segmented regions each having a stability score equal to or higher than a threshold value. In this situation, when the threshold value is "5", the determining function 162 determines at least one measurement ROI having an arbitrary shape, from within the region combining together the plurality of segmented regions indicated with the "black dots". Because the processes performed after the measurement ROI is determined are the same as those explained in the embodiments above, explanations thereof will be omitted.

The configuration illustrated in FIG. 14 is merely an example. Possible embodiments are not limited to the example illustrated in FIG. 14. For instance, although FIG. 14 illustrates the example in which the measurement ROI is determined from within the region combining together the segmented regions indicated with the "black dots", possible embodiments are not limited to this example. For instance, the determining function 162 may determine a measurement ROI from within a region combining together the segmented regions indicated with the "black dots" and the "white dots". In other words, the stability scores to be used for determining the measurement ROI may arbitrarily be set by the operator.

Further, although FIG. 14 illustrates the example in which the stability scores are evaluated in the three grades, possible embodiments are not limited to this example. For instance, the index value calculating function 161 may evaluate the stability scores in two grades or in four or more grades. In other words, the operator may arbitrarily set the number of grades in which the stability scores are evaluated.

Further, although FIG. 14 illustrates the example in which the measurement ROI is determined, possible embodiments are not limited to this example. For instance, the determining function 162 may determine a measurement candidate ROI instead of the measurement ROI, as explained in the second embodiment.

An Evaluation Using Multiple Grades

Further, for instance, although in the embodiment above (FIG. 3), the example is explained in which the magnitude of the variance is evaluated in the two grades (whether the variance is large or small) while using only the one threshold value, possible embodiments are not limited to this example. For instance, when making a judgment by using two threshold values, the index value calculating function 161 may evaluate the variance in three grades such as "Recommended", "Passable", and "Not Recommended", as illustrated in FIG. 14. In that situation, a measurement ROI may be determined by using the "Recommended" regions, similarly to the example in FIG. 14. Alternatively, a measurement ROI may be determined by using the "Recommended" and the "Passable" regions. In another example, the index value calculating function 161 may make an evaluation in four or more grades by using three or more threshold values.

The Analyzing Apparatus

Further, for example, in the embodiments described above, the ultrasound diagnosis apparatus is explained as an example of the analyzing apparatus. However, possible embodiments are not limited to this example. For instance, as the analyzing apparatus, other medical image diagnosis apparatuses besides the ultrasound diagnosis apparatus 1 are also applicable, such as X-ray diagnosis apparatuses, X-ray CT apparatuses, MRI apparatuses, SPECT apparatuses, PET apparatuses, SPECT-CT apparatuses in which a SPECT apparatus and an X-ray CT apparatus are integrated together, PET-CT apparatuses in which a PET apparatus and an X-ray CT apparatus are integrated together, or a group made up of any of these apparatuses. Further, as the analyzing apparatus, not only medical image diagnosis apparatuses, but also arbitrary information processing apparatuses (computers) capable of processing medical information are applicable.

Figure 15:
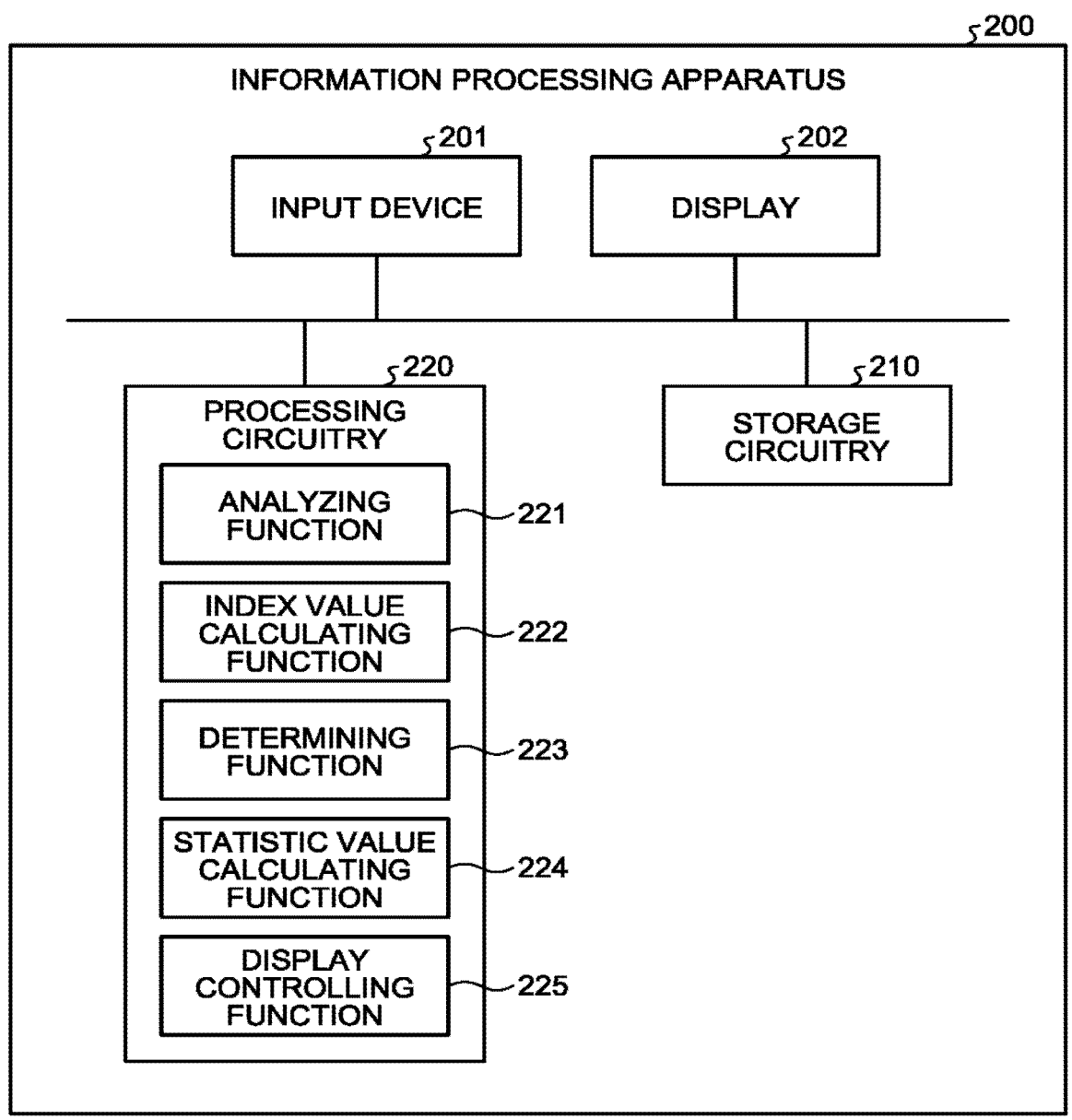
FIG. 15 is a block diagram illustrating an exemplary configuration of an information processing apparatus according to yet another embodiment.

FIG. 15 is a block diagram illustrating an exemplary configuration of an information processing apparatus 200 according to yet another embodiment. The information processing apparatus 200 is, for example, an apparatus such as a personal computer or a workstation.

As illustrated in FIG. 15, the information processing apparatus 200 includes an input device 201, a display 202, a storage circuitry 210, and a processing circuitry 220. The input device 201, the display 202, the storage circuitry 210, and the processing circuitry 220 are connected to one another so as to be able to communicate with one another.

The input device 201 is an input device such as a mouse, a keyboard, a touch panel, and/or the like, configured to receive various types of instructions and setting requests from the operator. The display 202 is a display device configured to display medical images and a GUI used by the operator to input the various types of setting requests through the input device 201.

The storage circuitry 210 may be, for example, a NOT-AND (NAND) flash memory or a Hard Disk Drive (HDD) and is configured to store therein various types of programs used for displaying medical image data and the GUI as well as information used by the programs.

The processing circuitry 220 an electronic device (a processor) configured to control the entirety of processes performed by the information processing apparatus 200. The processing circuitry 220 executes an analyzing function 221, an index value calculating function 222, a determining function 223, a statistic value calculating function 224, and a display controlling function 225. The processing functions executed by the processing circuitry 220 are, for example, recorded in the storage circuitry 210 in the form of computer-executable programs. By reading and executing the programs, the processing circuitry 220 is configured to realize the functions corresponding to the read programs.

For example, the analyzing function 221 is capable of performing basically the same processes as those performed by the analyzing function 121 illustrated in FIG. 1. The index value calculating function 222 is capable of performing basically the same processes as those performed by the index value calculating function 161 illustrated in FIG. 1. The determining function 223 is capable of performing basically the same processes as those performed by the determining function 162 illustrated in FIG. 1. The statistic value calculating function 224 is capable of performing basically the same processes as those performed by the statistic value calculating function 163 illustrated in FIG. 1. The display controlling function 225 is capable of performing basically the same processes as those performed by the display controlling function 164 illustrated in FIG. 1. With these arrangements, the information processing apparatus 200 is able to analyze the tissue characteristic with an excellent level of precision, similarly to the ultrasound diagnosis apparatus 1 explained above.

Tissue Characteristic Parameters

Further, for instance, in the embodiments described above, the example is explained in which the shear velocity values of the shear wave are used as an example of the tissue characteristic parameter values. However, possible embodiments are not limited to this example. For instance, instead of the shear velocity values of the shear wave, arrival times of the shear wave explained above may be used. Alternatively, elasticity modulus values may be used.

Further, for example, the ultrasound diagnosis apparatus 1 is able to use any of the following as a tissue characteristic parameter: "velocity" of a blood flow based on a color Doppler method; a "displacement" of a tissue based on a Tissue Doppler Imaging (TDI) method; a "strain" of a tissue based on strain elastography to express in an image a strain caused by small vibration to press and release a patient's tissue; an "attenuation" of an ultrasound wave propagating through a patient's body expressed as an attenuation image; and a "brightness local variance value" indicating a degree of deviation from a Rayleigh distribution representing a distribution of signal amplitudes of a reception signal. The analyzing function 121 calculates, as the tissue characteristic parameter values, one selected from among shear velocity values, arrival times, elasticity modulus values, velocity values, displacement values, strain values, attenuation values, and brightness local variance values, with respect to the positions where the scan was performed. Further, besides the tissue characteristic parameter obtained by the ultrasound diagnosis apparatus 1, it is possible to use, as a tissue characteristic parameter, a parameter indicating firmness levels based on elastography obtained by using an MRI apparatus or a parameter related to a substance identification scheme realized by a dual energy CT analysis that utilizes differences in an X-ray attenuation coefficient among various substances. In other words, it is possible to use any parameter as long as the parameter is not a parameter used in a tomographic image of a tissue in a patient's body, but is a parameter expressing a characteristic of a tissue.

Further, the constituent elements of the apparatuses and the devices illustrated in the drawings are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

With regard to the processes explained in the above embodiments, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, it is possible to realize the analyzing method explained in the above embodiments, by causing a computer such as a personal computer or a workstation to execute an analyzing computer program (hereinafter, "analyzing program") prepared in advance. It is possible distribute the analyzing program via a network such as the Internet. Further, the analyzing program may be executed as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

According to at least one aspect of the embodiments described above, it is possible to analyze the tissue characteristic with an excellent level of precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analyzing apparatus comprising processing circuitry configured:

to calculate, with respect to each of a plurality of positions within a region of interest for a scan performed when a shear wave propagates through a body of a patient, at least one of shear velocity values, arrival times, elasticity modulus values, velocity values, displacement values, and strain values, by analyzing a result of the scan performed on the patient;

to determine a measurement region in the region of interest based on the calculated values; and to calculate a statistic value of at least one of shear velocity values, arrival times, elasticity modulus values, velocity values, displacement values, and strain values in the measurement region.

2. The analyzing apparatus according to claim 1, wherein the processing circuitry calculates an index value related to variance among the calculated values with respect to each of a plurality of sub-regions included in the region of interest, and the processing circuitry determines the measurement region by comparing the index value of each of the plurality of sub-regions with a threshold value.

3. The analyzing apparatus according to claim 2, wherein the processing circuitry causes the sub-regions to be displayed into an image based on the calculated values.

4. The analyzing apparatus according to claim 2, wherein the processing circuitry receives an input to change a size of the sub-regions.

5. The analyzing apparatus according to claim 2, wherein the processing circuitry receives an input to change the threshold value.

6. The analyzing apparatus according to claim 5, wherein the processing circuitry determines the measurement region by comparing the index value of each of the plurality of sub-regions with the changed threshold value.

7. The analyzing apparatus according to claim 5, wherein the processing circuitry receives, as the input, an instruction of an operator to change the threshold value.

8. The analyzing apparatus according to claim 5, wherein the processing circuitry is further configured to re-determine a measurement region in the region of interest based on comparison between the changed threshold value and at least one of the calculated values.

9. The analyzing apparatus according to claim 8, wherein the processing circuitry is further configured to cause the re-determined measurement region to be displayed into an image based on the calculated values.

10. The analyzing apparatus according to claim 2, wherein the processing circuitry changes the threshold value in accordance with a site of the patient subject to a measuring process.

11. The analyzing apparatus according to claim 2, wherein, as the index value, the processing circuitry calculates one selected from among a variance value, a standard deviation, and a residual sum of squares, with respect to the calculated values.

12. The analyzing apparatus according to claim 2, wherein the processing circuitry determines the threshold value based on a site of the patient subject to the scan.

13. The analyzing apparatus according to claim 12, wherein an arrangement is acceptable in which an appropriate threshold value is registered in advance for each of various sites, and the processing circuitry determines the threshold value by reading a threshold value corresponding to the site designated by an operator.

14. The analyzing apparatus according to claim 1, wherein
the processing circuitry obtains distribution information of the calculated values with respect to each of a plurality of sub-regions included in the region of interest,
the processing circuitry calculates an index value indicating a degree of stability of the calculated values for each of the sub-regions, by using the distribution information as an input to a trained machine learning scheme, and
the processing circuitry determines the measurement region by comparing the index value of each of the plurality of sub-regions with a threshold value.

15. The analyzing apparatus according to claim 1, wherein the processing circuitry causes the measurement region to be displayed into an image based on the calculated values.

16. The analyzing apparatus according to claim 1, wherein, as the statistic value, the processing circuitry calculates one selected from among an average value, a median, a variance value, a standard deviation, and a residual sum of squares, with respect to the calculated values.

17. The analyzing apparatus according to claim 1, wherein the processing circuitry calculates, by analyzing a result of a MRI scan performed on the patient, at least one of the shear velocity values, the arrival times, the elasticity modulus values, the velocity values, the displacement values, and the strain values.

18. The analyzing apparatus according to claim 1, wherein the scan is performed such that an ultrasound probe transmits an observation-purpose pulse in order to observe the shear wave caused by a push pulse transmitted from the ultrasound probe.

19. An analyzing apparatus comprising processing circuitry configured:
to calculate, with respect to each of a plurality of positions within a region of interest for a scan performed when a shear wave propagates through a body of a patient, at least one of shear velocity values, arrival times, elasticity modulus values, velocity values, displacement values, and strain values, by analyzing a result of the scan performed on the patient;
to determine a measurement candidate region in the region of interest based on the calculated values; and
to cause the measurement candidate region to be displayed into an image.

20. The analyzing apparatus according to claim 19, wherein
the processing circuitry calculates an index value related to variance among the calculated values, with respect to each of a plurality of sub-regions included in the region of interest, and
the processing circuitry determines the measurement candidate region by comparing the index value of each of the plurality of sub-regions with a threshold value.

21. The analyzing apparatus according to claim 20, wherein the processing circuitry causes the sub-regions to be displayed into the image based on the calculated values.

22. The analyzing apparatus according to claim 20, wherein the processing circuitry determines one or more measurement candidate regions, from within a region combining together two or more of the sub-regions that are each determined, as a result of the comparison, to have a small value as the variance.

23. The analyzing apparatus according to claim 22, wherein the processing circuitry determines one or more measurement candidate regions of which a quantity is determined in advance.

24. The analyzing apparatus according to claim 22, wherein, as the measurement candidate region, the processing circuitry determines a circular region having a largest diameter.

25. The analyzing apparatus according to claim 19, wherein
the processing circuitry obtains distribution information of the calculated values with respect to each of a plurality of sub-regions included in the region of interest,
the processing circuitry calculates an index value indicating a degree of stability of the calculated values for each of the sub-regions, by using the distribution information as an input to a trained machine learning scheme, and
the processing circuitry determines the measurement candidate region by comparing the index value of each of the plurality of sub-regions with a threshold value.

26. The analyzing apparatus according to claim 25, wherein the processing circuitry determines one or more measurement candidate regions from within a region combining together two or more of the sub-regions that are each determined, as a result of the comparison, to exhibit a high level as the degree of stability.

27. The analyzing apparatus according to claim 19, wherein the processing circuitry determines the measurement candidate region having a shape and a size that are set in advance.

28. The analyzing apparatus according to claim 19, wherein the image is at least one of B-mode image, a firmness image, and a region image in which firmness levels of tissue in the body of the patient are displayed.

29. The analyzing apparatus according to claim 19, wherein the scan is performed such that an ultrasound probe transmits an observation-purpose pulse in order to observe the shear wave caused by a push pulse transmitted from the ultrasound probe.

30. An analyzing method comprising:
calculating, with respect to each of a plurality of positions within a region of interest for a scan performed when a shear wave propagates through a body of a patient, at least one of shear velocity values, arrival times, elasticity modulus values, velocity values, displacement values, and strain values, by analyzing a result of the scan performed on the patient;
determining a measurement region in the region of interest based on the calculated values; and
calculating a statistic value of at least one of shear velocity values, arrival times, elasticity modulus values, velocity values, displacement values, and strain values in the measurement region.

31. The analyzing method according to claim 30, wherein the scan is performed such that an ultrasound probe transmits an observation-purpose pulse in order to observe the shear wave caused by a push pulse transmitted from the ultrasound probe.

32. An analyzing method comprising:
calculating, with respect to each of a plurality of positions within a region of interest for a scan performed when a shear wave propagates through a body of a patient, at least one of shear velocity values, arrival times, elasticity modulus values, velocity values, displacement values, and strain values, by analyzing a result of the scan performed on the patient;
determining a measurement candidate region in the region of interest based on the calculated values: and causing the measurement candidate region to be displayed into an image.

33. The analyzing method according to claim 32, wherein the scan is performed such that an ultrasound probe transmits an observation-purpose pulse in order to observe the shear wave caused by a push pulse transmitted from the ultrasound probe.

34. An analyzing apparatus comprising processing circuitry configured:
to calculate, with respect to each of a plurality of positions within a region of interest for a scan performed when a shear wave propagates through a body of a patient, parameter values based on a shear wave, by analyzing a result of the scan performed on the patient;
to determine a measurement region in the region of interest based on the calculated values; and
to calculate a statistic value of the parameter values in the measurement region.

35. The analyzing apparatus according to claim 34, wherein the scan is performed such that an ultrasound probe transmits an observation-purpose pulse in order to observe the shear wave caused by a push pulse transmitted from the ultrasound probe.

36. An analyzing apparatus comprising processing circuitry configured:
to calculate, with respect to each of a plurality of positions within a region of interest for a scan performed when a shear wave propagates through a body of a patient, parameter values based on a shear wave, by analyzing a result of the scan performed on the patient;
to determine a plurality of measurement candidate regions in the region of interest based on the calculated values; and
to select a measurement region from the plurality of measurement candidate regions.

37. The analyzing apparatus according to claim 36, wherein the scan is performed such that an ultrasound probe transmits an observation-purpose pulse in order to observe the shear wave caused by a push pulse transmitted from the ultrasound probe.

* * * * *